United States Patent
Fujii et al.

(10) Patent No.: US 11,079,276 B2
(45) Date of Patent: Aug. 3, 2021

(54) IMAGING DEVICE PROVIDED WITH LIGHT SOURCE THAT EMITS PULSED LIGHT AND IMAGE SENSOR

(71) Applicant: Panasonic Intellectual Property Management Co., Ltd., Osaka (JP)

(72) Inventors: Toshiya Fujii, Shiga (JP); Takamasa Ando, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

(21) Appl. No.: 16/245,107

(22) Filed: Jan. 10, 2019

(65) Prior Publication Data

US 2019/0162596 A1    May 30, 2019

Related U.S. Application Data

(63) Continuation of application No. 15/188,071, filed on Jun. 21, 2016, now Pat. No. 10,215,636.

(30) Foreign Application Priority Data

Jul. 2, 2015  (JP) ................ 2015-133891

(51) Int. Cl.
*G01J 3/28* (2006.01)
*G01N 21/65* (2006.01)
(Continued)

(52) U.S. Cl.
CPC ......... *G01J 3/2823* (2013.01); *A61B 5/0075* (2013.01); *G01B 11/24* (2013.01); *G01J 3/0229* (2013.01);
(Continued)

(58) Field of Classification Search
CPC ................................. G01J 3/2823
See application file for complete search history.

(56) References Cited

U.S. PATENT DOCUMENTS 5,627,639 A   5/1997  Mende et al.
7,336,353 B2  2/2008  Brady et al.
(Continued)

FOREIGN PATENT DOCUMENTS

JP  2005-091343 A  4/2005
JP  2008-096241 A  4/2008
(Continued)

OTHER PUBLICATIONS

Notice of Allowance issued in related U.S. Appl. No. 15/188,071 dated Oct. 19, 2018.
(Continued)

*Primary Examiner* — Yara B Green
(74) *Attorney, Agent, or Firm* — McDermott Will & Emery LLP

(57) ABSTRACT

An optical filter including filter regions arrayed two-dimensionally, in which the filter regions include a first region and a second region; a wavelength distribution of an optical transmittance of the first region has a first local maximum in a first wavelength band and a second local maximum in a second wavelength band that differs from the first wavelength band, and a wavelength distribution of an optical transmittance of the second region has a third local maximum in a third wavelength band that differs from each of the first wavelength band and the second wavelength band and a fourth local maximum in a fourth wavelength band that differs from the third wavelength band.

6 Claims, 19 Drawing Sheets

(51) Int. Cl.
*A61B 5/00* (2006.01)
*G01J 3/02* (2006.01)
*G01N 21/64* (2006.01)
*G01N 21/47* (2006.01)
*G01J 3/12* (2006.01)
*G01B 11/24* (2006.01)
*G01S 17/89* (2020.01)

(52) U.S. Cl.
CPC ........... *G01J 3/2803* (2013.01); *G01J 3/2846* (2013.01); *G01J 3/2889* (2013.01); *G01N 21/65* (2013.01); *G01S 17/89* (2013.01); *A61B 5/0042* (2013.01); *G01J 2003/1213* (2013.01); *G01J 2003/2826* (2013.01); *G01N 21/64* (2013.01); *G01N 2021/4797* (2013.01)

(56) References Cited

U.S. PATENT DOCUMENTS

| | | |
|---|---|---|
| 2004/0021078 A1 | 2/2004 | Hagler |
| 2005/0283071 A1 | 12/2005 | Ripoll et al. |
| 2006/0038705 A1 | 2/2006 | Brady et al. |
| 2006/0092414 A1 | 5/2006 | Geshwind et al. |
| 2006/0192938 A1 | 8/2006 | Kawahito |
| 2007/0097363 A1 | 5/2007 | Brady et al. |
| 2008/0095298 A1 | 4/2008 | Shefsky |
| 2008/0266564 A1* | 10/2008 | Themelis ............. G01J 3/2823 356/419 |
| 2009/0020714 A1 | 1/2009 | Slinger |
| 2010/0253941 A1 | 10/2010 | Brady et al. |
| 2010/0302660 A1* | 12/2010 | Hirokubo ............. G02B 26/001 359/850 |
| 2012/0162638 A1 | 6/2012 | Villeneuve |
| 2012/0327248 A1 | 12/2012 | Tack et al. |
| 2013/0016284 A1* | 1/2013 | Mestha ............... G06T 5/50 348/571 |
| 2013/0083224 A1* | 4/2013 | Tai ............... H04N 9/04557 348/280 |
| 2014/0163391 A1 | 6/2014 | Koizumi et al. |
| 2014/0253713 A1 | 9/2014 | Zhai et al. |
| 2014/0374573 A1 | 12/2014 | Arce et al. |
| 2015/0177429 A1* | 6/2015 | Darty ............. A61B 5/0075 348/342 |
| 2016/0148344 A1 | 5/2016 | Koga |
| 2017/0234726 A1 | 8/2017 | Ockenfuss |

FOREIGN PATENT DOCUMENTS

| | | |
|---|---|---|
| JP | 2008-149154 A | 7/2008 |
| JP | 2009-529160 A | 8/2009 |
| JP | 2010-071832 A | 4/2010 |
| JP | 2012-125370 A | 7/2012 |
| JP | 2013-244343 A | 12/2013 |
| JP | 2014-531032 A | 11/2014 |
| WO | 2001/061291 A1 | 8/2001 |
| WO | 2006/078687 A2 | 7/2006 |
| WO | 2013/002350 A1 | 1/2013 |
| WO | 2014/147515 A1 | 9/2014 |
| WO | 2016012980 A1 | 1/2016 |

OTHER PUBLICATIONS

Non-Final Office Action issued in related U.S. Appl. No. 15/188,071 dated Apr. 27, 2018.

* cited by examiner

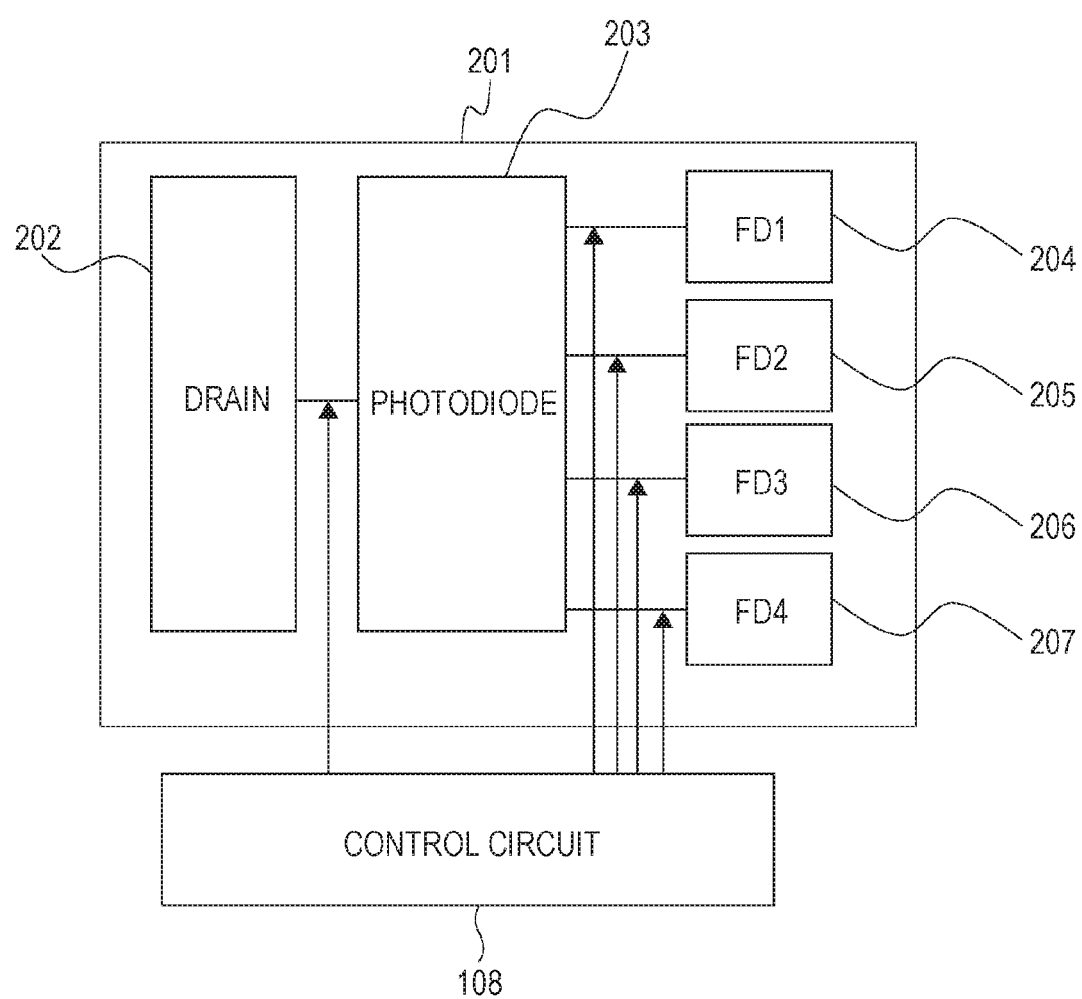

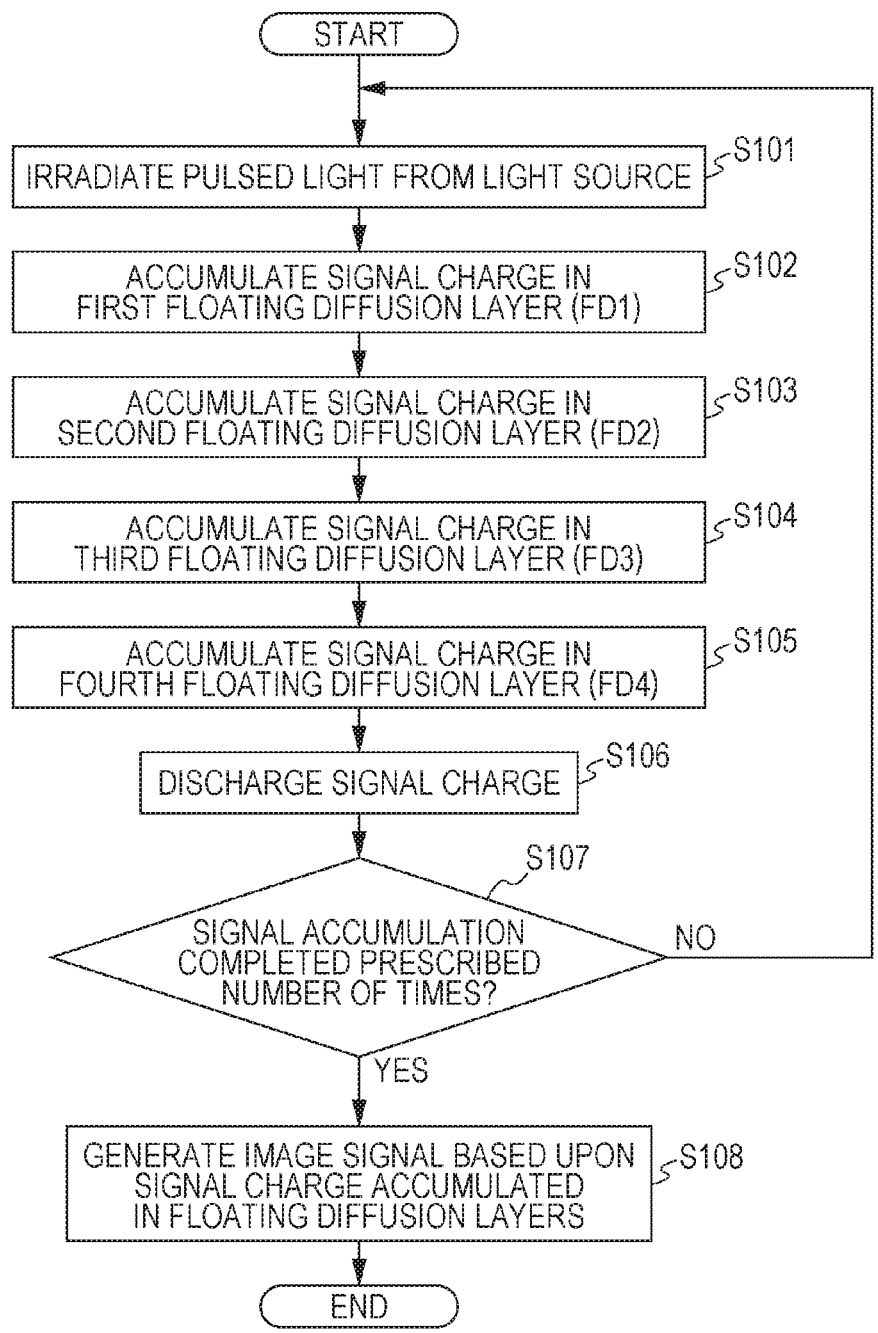

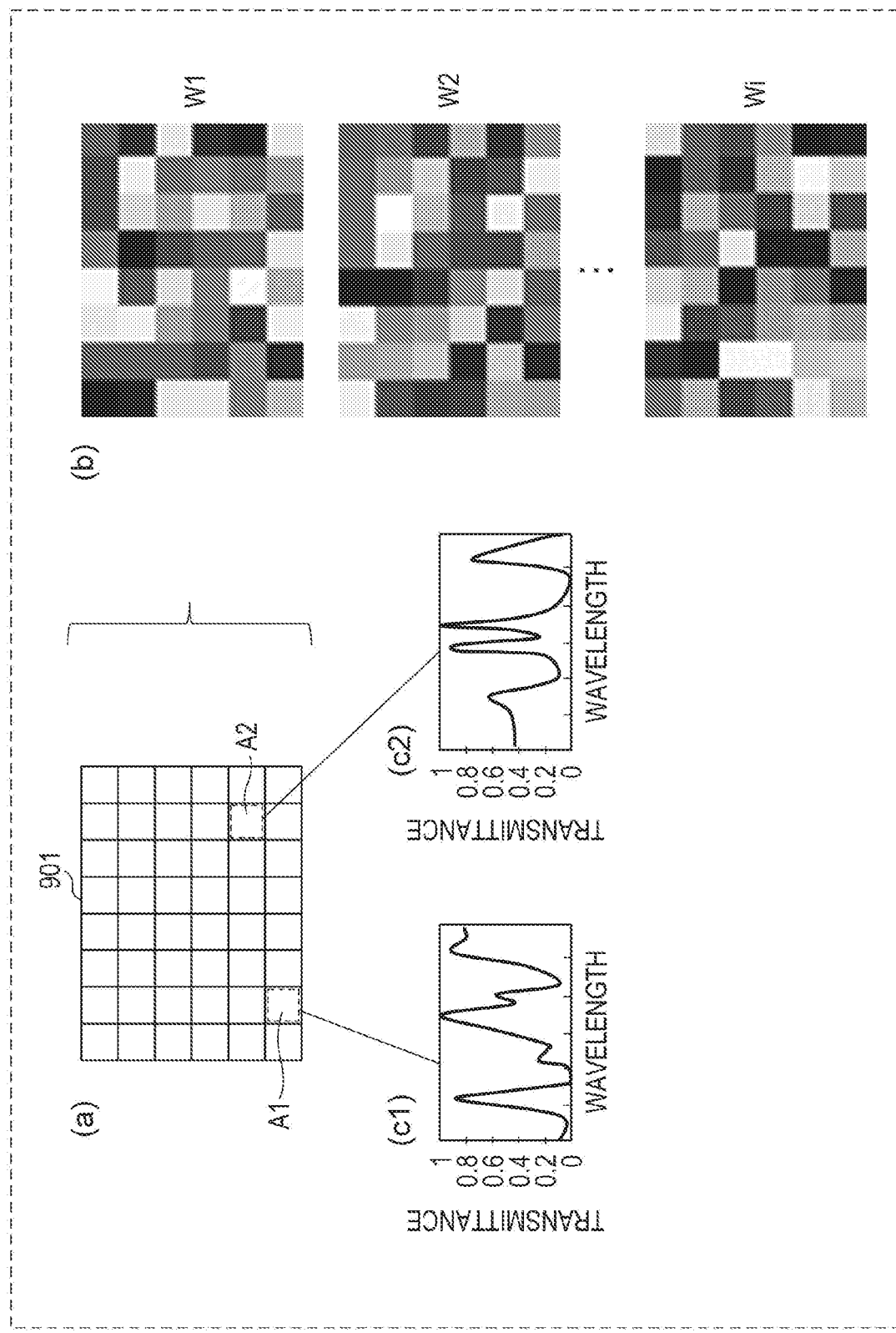

IMAGING DEVICE PROVIDED WITH LIGHT SOURCE THAT EMITS PULSED LIGHT AND IMAGE SENSOR

CROSS REFERENCE

This application is the Continuation of U.S. patent application Ser. No. 15/188,071 filed on Jun. 21, 2016, now U.S. Pat. No. 10,215,636, which claims the benefit of Japanese Application No. 2015-133891 filed on Jul. 2, 2015, the entire contents of each are hereby incorporated by reference.

BACKGROUND

1. Technical Field

The present disclosure relates to an imaging device that acquires internal information of a target such as a gas or a living body.

2. Description of the Related Art

In applications such as the detection of gas leakages, biometry, and material analysis, methods are used in which light (including visible light, infrared rays, or ultraviolet rays) is irradiated onto a target, and the transmitted light, reflected light, or scattered light therefrom is detected to thereby acquire internal information of the target.

Examples of imaging systems in which such methods are used are disclosed in Japanese Unexamined Patent Application Publication No. 2005-91343, Japanese Unexamined Patent Application Publication No. 2008-149154, International Publication No. 2013/002350, and the specification of U.S. Pat. No. 7,283,231, for example.

SUMMARY

In one general aspect, the techniques disclosed here feature an optical filter including filter regions arrayed two-dimensionally, wherein the filter regions include a first region and a second region; a wavelength distribution of an optical transmittance of the first region has a first local maximum in a first wavelength band and a second local maximum in a second wavelength band that differs from the first wavelength band, and a wavelength distribution of an optical transmittance of the second region has a third local maximum in a third wavelength band that differs from each of the first wavelength band and the second wavelength band and a fourth local maximum in a fourth wavelength band that differs from the third wavelength band.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3 is a drawing depicting a schematic configuration example of one pixel of an image sensor in embodiment 1 of the present disclosure;

FIG. 4 is a flowchart depicting an imaging operation in embodiment 1 of the present disclosure;

FIG. 10 is a drawing schematically depicting a configuration of an encoding spectroscopic element in embodiment 2 of the present disclosure;

Figure 1:
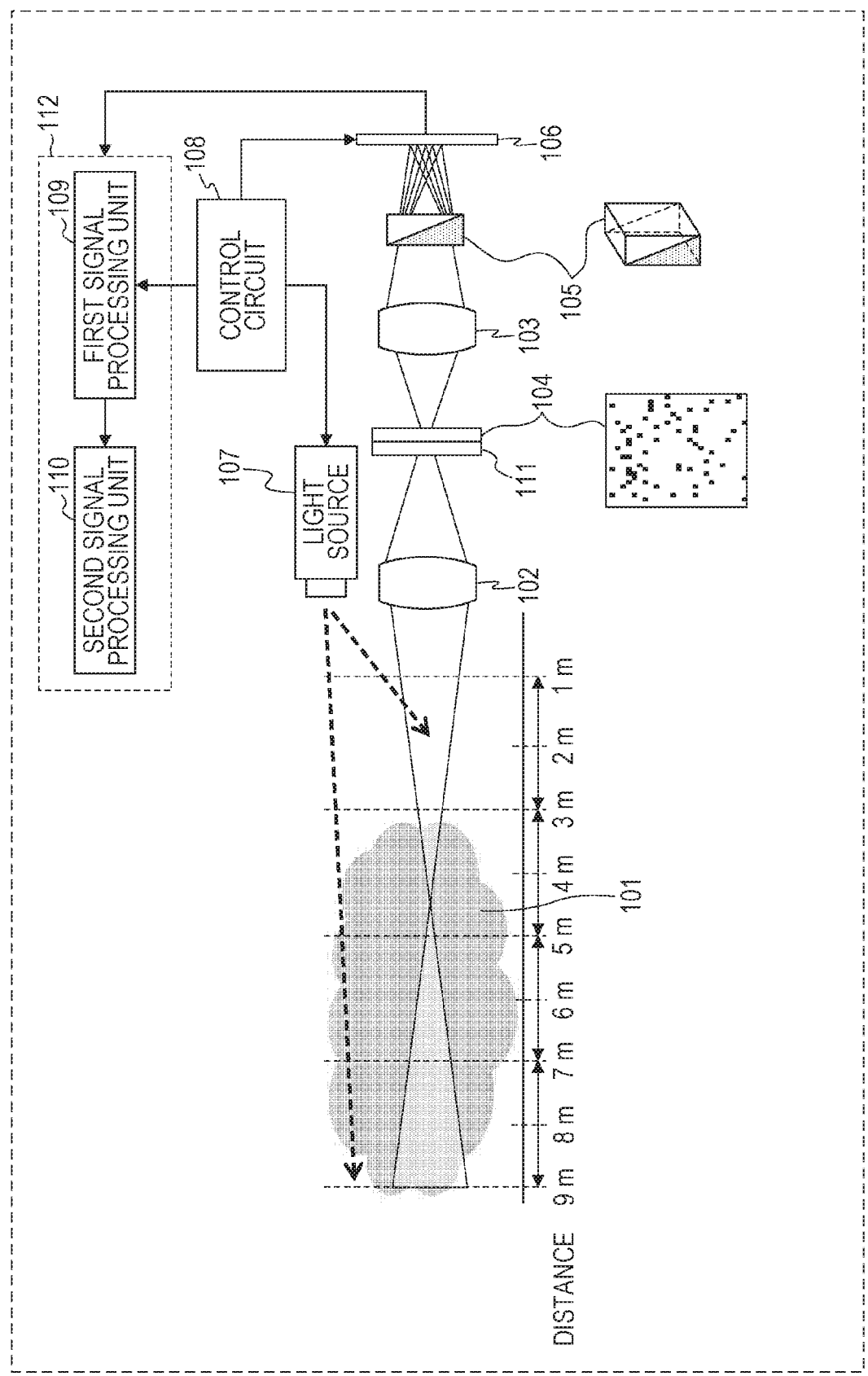
FIG. 1 is a drawing schematically depicting a configuration of an imaging device in embodiment 1 of the present disclosure.

DETAILED DESCRIPTION (Findings Forming the Basis for the Present Disclosure)

Prior to describing embodiments of the present disclosure, the findings forming the basis for the present disclosure will be described.

The present inventors discovered the following problems with regard to conventional gas leakage detection systems and biological information detection systems.

In a conventional common gas leakage detection system, suctioned gas is brought into direct contact with a sensor, and the concentration of a detection-target gas is measured on the basis of changes in physical quantities such as electric resistance and current values within the sensor. However, in a method such as this, it is necessary to bring a gas into direct contact with the sensor, and it is therefore not possible to detect a gas in a location away the sensor. In addition, there is a drawback in that there are many uncertainties due to environmental conditions such as the wind direction and the installation location.

Japanese Unexamined Patent Application Publication No. 2005-91343 discloses an example of a gas detection system with which this kind of drawback is resolved. In the system of Japanese Unexamined Patent Application Publication No. 2005-91343, ultraviolet laser light is irradiated onto a gas to cause Raman scattering. Raman scattering is a phenomenon in which scattered light having a wavelength that is different from the wavelength of the light incident on molecules is generated. This phenomenon occurs due to the molecules receiving light and entering a temporary high-energy intermediary state, and thereafter transitioning to a vibrationally excited state or a ground state. In the case where a transition is made from the ground state to the vibrationally excited state via the intermediary state, scattered light having a longer wavelength than the incident light is generated. This wavelength shift is called a Stokes shift. Conversely, in the case where a transition is made from the vibrationally excited state to the ground state via the intermediary state, scattered light having a shorter wavelength than the incident light is generated. This wavelength shift is called an anti-Stokes shift.

In the system of Japanese Unexamined Patent Application Publication No. 2005-91343, a leakage of a gas and the type thereof are detected in a non-contact manner by detecting the Stokes shift of Raman scattered light. A gas leakage can be displayed as a two-dimensional image by superimposing an image depicting the distribution of the detected gas onto a visible image of a monitoring-target space. It is described that it is thereby possible to safely monitor gas leakages and specify leakage locations remotely.

Japanese Unexamined Patent Application Publication No. 2005-91343 describes that a photographing timing is changed according to the distance range of a detection target. Photographing at a single distance range is possible by means of brief exposure synchronized with light emission by a light source. However, it is not possible to perform photographing at a plurality of distance ranges at the same time.

In the embodiments of the present disclosure, it is possible to perform photographing at a plurality of distance ranges using a method referred to as "time-resolved imaging". Hereinafter, the time-resolved imaging used in the embodiments of the present disclosure will be described.

With the progress of laser light irradiation technology, it has become possible to repeatedly irradiate a target with extremely brief pulsed light of the order of nanoseconds (ns) to picoseconds (ps), and to control, at high speed, the light reception time of an image sensor in synchronization therewith. This kind of imaging that is performed with a light source and an image sensor being controlled at high speed is referred to as "time-resolved imaging". As a representative application example, measurement imaging devices that use a method referred to as time of flight (TOF) in which the distance to a subject is detected in pixel units on the basis of the flight time of light have been commercialized.

Due to the application of time-resolved imaging, for phenomena that repeatedly occur in a similar manner when light is emitted, it has also become possible for extremely brief light reception to be repeated in conjunction with light emission to accumulate signals, and for brief changes in phenomena to be reproduced as video. For example, it has also become possible to visualize, as video, the way in which light propagates.

Time-resolved imaging technology is being considered for application not only for spaces through which light is transmitted but also for light scattering bodies such as living bodies. For example, in time-resolved diffuse optical tomography, a near infrared ray of two wavelengths having a relatively low light absorption rate with respect to both water and hemoglobin is used to form a tomographic image from the concentration distribution of oxidized hemoglobin and deoxidized hemoglobin within a living body.

Particularly in the case where a living body is to be a target, noninvasive biological observation without any exposure to radiation whatsoever is possible by using infrared rays (also referred to as "infrared light" hereinafter) that are safe for living bodies, compared with roentgen and X-ray CT widely used as diagnostic imaging methods. Furthermore, imaging by near-infrared light is suitable for reducing device size and weight and reducing cost compared with an MRI device, for example, for which nuclear magnetic resonance is used. Thus, imaging by near-infrared light has begun to be widely used in cutting-edge research relating to elucidating the functions of biological tissue.

However, near-infrared light scatters to a considerably high degree when passing through biological tissue, and as a result, severe light scattering occurs within the biological tissue. There is a problem in that this light scattering causes a considerable decline in the spatial resolution of imaging.

One known method for solving this problem is an image reconstruction algorithm in which: an optical characteristic value (absorption coefficient and scattering coefficient, for example) spatial distribution serving as a scattering body is assumed for detection-target biological tissue to numerically calculate light propagation within the scattering body (forward problem); and the result thereof and data actually obtained by time-resolved imaging are compared, and the assumption of the spatial distribution is repeated until both match (inverse problem). By using an algorithm such as this, it is possible to reconstruct a three-dimensional image having improved spatial resolution.

Conventional time-resolved diffuse optical tomography is useful in applications such as research regarding activation of the brain and optical mammography for screening for breast cancer. However, a light source of two or three restricted wavelengths is used, and it is therefore not possible to acquire spectral information of a large number of bands. Consequently, it is not possible to detect information of molecules having high specificity from living tissue.

Japanese Unexamined Patent Application Publication No. 2008-149154 discloses an example of a system that detects information of molecules having high specificity from living tissue. The system disclosed in Japanese Unexamined Patent Application Publication No. 2008-149154 includes: a near-infrared light source that provides incident light; a multipoint incident light irradiation array for guiding light into a living body from two or more separate excitation points; a plurality of optical fibers for transmitting light from the light source to each point of the multipoint incident light irradiation array; a multipoint detection array for collecting fluorescence emitted from a target from two or more separate collection points; a two-dimensional light emission array for transmitting light emitted from the target to a detector; a plurality of optical fibers for transmitting light from each collection point to a corresponding point on the two-dimensional light emission array; and the detector for detecting the light emitted from each point of the two-dimensional light emission array and converting into a digital signal corresponding to the light emitted from the target. It is described that, according to this kind of configuration, it is possible to acquire, with a high degree of high sensitivity, three-dimensional location information of abnormal molecules constituting the cause of a disease.

However, Japanese Unexamined Patent Application Publication No. 2008-149154 does not describe an imaging method with which information of a plurality of distance ranges is acquired with single-frame imaging.

The imaging device according to the embodiments of the present disclosure acquires information of a plurality of distance ranges with single-frame imaging, and also acquires information of a plurality of wavelengths. A technique referred to as compressed sensing is used to acquire information of a plurality of wavelengths. Hereinafter, compressed sensing will be described.

By utilizing spectral information of a large number of bands (several tens of bands or more, for example) that are each a narrow band, it is possible to comprehend detailed physical properties of an observation object not possible with a conventional RGB image. A camera that acquires this multi-wavelength information is referred to as a "hyperspectral camera". Hyperspectral cameras are used in various fields such as food inspection, biological inspection, pharmaceutical product development, and mineral component analysis. For example, International Publication No. 2013/002350 discloses a device that distinguishes between tumorous sites and non-tumorous sites of a subject by generating an image acquired with the wavelengths of the observation target being restricted to narrow bands. This device, by irradiating excitation light, detects the emission of 635-nm fluorescence by protoporphyrin IX that is accumulated in cancer cells, and the emission of 675-nm fluorescence by photo-protoporphyrin. Tumorous sites and non-tumorous sites are thereby identified.

The specification of U.S. Pat. No. 7,283,231 discloses an example of a hyperspectral camera in which compressed sensing is used. A device disclosed in the specification of U.S. Pat. No. 7,283,231 diffracts light from a measurement target with a first spectroscopic element such as a prism, and then implements marking with an encoding mask, and, in addition, restores the path of light rays with a second spectroscopic element. Thus, an image that has been encoded and multiplexed with respect to the wavelength axis is acquired by a sensor. By applying compressed sensing, a plurality of multi-wavelength images are reconstructed from the multiplexed image.

Compressed sensing is a technique for restoring a larger amount of data from acquired data of which there is a small number of samples. If the two-dimensional coordinates of a measurement target are taken as (x, y) and the wavelength is taken as $\lambda$, the desired data f is three-dimensional data of x, y, $\lambda$. In contrast to this, image data g obtained by a sensor is two-dimensional data that has been compressed and multiplexed in the $\lambda$ axis direction. The problem of obtaining the data f having a relatively large data amount from the acquired image g having a relatively small data amount is what is referred to as an ill-posed problem, and cannot be solved as it is. However, natural image data generally has redundancy, and by using this skillfully it is possible to convert this ill-posed problem into a well-posed problem. JPEG compression is an example of a technique for reducing the amount of data by using the redundancy of an image. JPEG compression uses a method in which image information is converted into frequency components, and non-essential portions of the data such as portions having low visual recognizability are removed. In compressed sensing, this kind of technique is incorporated into calculation processing, and desired data spaces are converted into spaces indicated by redundancy to thereby reduce unknowns and obtain a solution. For this conversion, a discrete cosine transform (DCT), wavelet transform, Fourier transform, total variation (TV), or the like is used.

The specification of U.S. Pat. No. 7,283,231 discloses a compressed sensing technique such as the aforementioned, but does not disclose a method for simultaneously acquiring information of a plurality of wavelengths, spatial distribution information, and information of a plurality of times (distance ranges).

With conventional techniques, it has been extremely difficult to simultaneously perform time-resolved imaging and spectroscopic imaging without sacrificing spatial resolution. An imaging device with which these are simultaneously achieved does not exist at the present time. In order to acquire information of a plurality of wavelengths, there has only been a method in which light sources having different light emission wavelengths are made to irradiate in a time-divided manner, and a method in which detectors are separated for each wavelength of a detection target. Simultaneity is sacrificed with the former, and spatial resolution is sacrificed with the latter.

The present inventors discovered the aforementioned problems in the conventional techniques, and carried out a diligent investigation into methods for solving these problems. As a result, it was found that it becomes possible to acquire information of a plurality of distance ranges and information of a plurality of wavelengths without sacrificing spatial resolution by using: a light source that emits pulsed light including components of a plurality of wavelengths; a time-resolved image sensor that detects light that is incident from a target, at high speed and in a time-divided manner; and an encoding element that modulates the intensity of the light that is incident on the image sensor, in accordance with location. If safe infrared light is used with respect to a living body in particular, imaging that is noninvasive and with which there is no exposure to radiation such as with X-rays is possible. Hereinafter, an example of an imaging device having such a configuration will be described.

The present disclosure includes imaging devices according to the following items.

[Item 1]

An imaging device, provided with:

a light source that, in operation, emits pulsed light including components of different wavelengths;

an encoding element that has regions each having different light transmittance, through which incident light from a target onto which the pulsed light has been irradiated is transmitted;

a spectroscopic element that, in operation, causes the incident light transmitted through the regions to be dispersed into light rays in accordance with the wavelengths; and an image sensor that, in operation, receives the light rays dispersed by the spectroscopic element.

[Item 2]
An imaging device, provided with:
a light source that, in operation, emits pulsed light including components of different wavelengths;
an encoding spectroscopic element that has regions each having different wavelength distributions of light transmittance, through which incident light from a target onto which the pulsed light has been irradiated is transmitted; and
an image sensor that, in operation, receives the incident light transmitted through the regions.

[Item 3]
The imaging device according to item 1 or 2, further comprising:
a control circuit, wherein:
the target has a first portion and a second portion; and
the control circuit,
at a first time, causes the light source to emit the pulsed light,
at a second time subsequent to the first time, causes the image sensor to accumulate first signal charge that is based upon first incident light from the first portion of the target,
at a third time subsequent to the second time, causes the image sensor to accumulate second signal charge that is based upon second incident light from the second portion of the target,
and causes the image sensor to output a first image signal that is based upon the first signal charge and a second image signal that is based upon the second signal charge.

[Item 4]
The imaging device according to item 3, wherein:
the image sensor includes photodetection cells that each include a first charge accumulator and a second charge accumulator; and
the control circuit,
at the second time, causes the first charge accumulator in each of the photodetection cells to accumulate the first signal charge,
and, at the third time, causes the second charge accumulator in each of the photodetection cells to accumulate the second signal charge.

[Item 5]
The imaging device according to item 3 or 4,
wherein the control circuit,
after causing the light source and the image sensor to repeat, more than once, the emitting of the pulsed light at the first time, the accumulating of the first signal charge at the second time, and the accumulating of the second signal charge at the third time,
causes the image sensor to output the first image signal and the second image signal.

[Item 6]
The imaging device according to any of items 3 to 5, further provided with:
a signal processing circuit that, in operation, separates the first image signal into first separate image signals in accordance with the wavelengths, and separates the second image signal into second separate image signals in accordance with the wavelengths.

[Item 7]
The imaging device according to item 6,
wherein, in operation, the signal processing circuit generates a three-dimensional image of the target on the basis of the first separate image signals and the second separate image signals.

[Item 8]
The imaging device according to item 7, wherein:
the target is a light scattering body; and,
in operation, the signal processing circuit
assumes an optical characteristic value distribution for the target,
calculates light propagation within the target,
compares a calculation result for the light propagation with the first separate image signals and the second separate image signals,
repeatedly assumes the optical characteristic value distribution until a comparison result indicates matching, and
generates the three-dimensional image on the basis of the optical characteristic value distribution from when the comparison result indicates matching.

[Item 9]
The imaging device according to any of items 1 to 8,
wherein the target is a gas.

[Item 10]
The imaging device according to any of items 1 to 7,
wherein the target is a light scattering body.

[Item 11]
The imaging device according to any of items 1 to 10,
wherein the pulsed light is an ultraviolet ray or an infrared ray.

[Item 12]
An imaging device, comprising:
a first light source that, in operation, emits first pulsed light including a first wavelength;
a second light source that, in operation, emits second pulsed light including a second wavelength that is different from the first wavelength;
an encoding element that has regions each having different light transmittance, through which incident light from a target onto which the first pulsed light and the second pulsed light are irradiated is transmitted;
a spectroscopic element that, in operation, causes the incident light transmitted through the regions to be dispersed into first incident light including the first wavelength and second incident light including the second wavelength; and
an image sensor that, in operation, receives the first incident light and the second incident light. The imaging device according to item 12 may further comprises a control circuit that at a first time, causes the first light source to emit the first pulsed light, and, at a second time that is different from the first time, causes the second light source to emit the second pulsed light.

[Item 13]
An imaging device, comprising:
a first light source that, in operation, emits first pulsed light including a first wavelength;
a second light source that, in operation, emits second pulsed light including a second wavelength that is different from the first wavelength;
an encoding spectroscopic element that has regions each having different wavelength distributions of light transmittance, through which incident light from a target onto which the first pulsed light and the second pulsed light are irradiated is transmitted; and
an image sensor that, in operation, receives the incident light transmitted through the regions. The imaging device according to item 13 may further comprises a control circuit that, at a first time, causes the first light source to emit the first pulsed light, and, at a second time that is different from the first time, causes the second light source to emit the second pulsed light.

In the present disclosure, all or part of any of a unit, device, member or portion, or all or part of the functional blocks in the block diagrams may be implemented as one or more electronic circuits including a semiconductor device, a semiconductor integrated circuit (IC) or a large scale integration (LSI). The LSI or IC may be integrated into one chip, or may be a combination of a plurality of chips. For example, functional blocks other than a storage element may be integrated into one chip. The name used here is LSI or IC, but it may also be referred to as a system LSI, a very large scale integration (VLSI), or an ultra large scale integration (ULSI) depending on the degree of integration. A field-programmable gate array (FPGA) that can be programmed after manufacturing an LSI, or a reconfigurable logic device that allows reconfiguration of the connection relationship inside the LSI or the setup of circuit cells inside the LSI can also be used for the same purpose.

In addition, it is also possible for the functions or operations of all or part of the unit, device, member or portion to be implemented by means of software processing. In such a case, the software is recorded on one or more non-transitory recording mediums such as a ROM, an optical disk or a hard disk drive, and when the software is executed by a processor, the software causes the processor together with peripheral devices to execute the functions specified in the software. A system or device may be provided with such one or more non-transitory recording mediums on which the software is recorded, a processor, and necessary hardware devices such as an interface.

Hereafter, embodiments of the present disclosure will be described in detail with reference to the drawings. It should be noted that the embodiments described hereinafter all represent comprehensive or specific examples. The numerical values, the shapes, the materials, the constituent elements, the arrangement of the constituent elements, the mode of connection, the steps, and the order of the steps and so forth given in the following embodiments are examples and are not intended to restrict the present disclosure. The various aspects described in the present specification may be combined with each other provided there are no resulting inconsistencies. Furthermore, constituent elements that are not described in the independent claims indicating the most significant concepts from among the constituent elements in the following embodiments are described as optional constituent elements. In the following description, constituent elements having substantially the same functions are denoted by common reference numerals, and descriptions thereof have been omitted.

Embodiment 1

FIG. 1 is a drawing schematically depicting a configuration of an imaging device in embodiment 1 of the present disclosure. FIG. 1 also depicts a detection target 101 as well as other constituent elements of the imaging device. This imaging device is able to detect the type and concentration of a gas constituting the detection target 101, and generate a three-dimensional (3D) image of the spatial distribution of the concentration of the gas.

The imaging device is provided with: a light source 107 that irradiates an ultraviolet ray having two wavelength components toward the target 101; an optical system (an image-forming optical system 102, an excitation light cut filter 111, an encoding element 104, a relay optical system 103, and a spectroscopic element 105) that is arranged in the optical path of light that is incident from the target 101; an image sensor 106 that detects light that has passed through the spectroscopic element 105; and a control circuit 108 that controls the light source 107 and the image sensor 106. A signal processing circuit 112 that processes image signals that are output from the image sensor 106 is also drawn in FIG. 1. The signal processing circuit 112 may be incorporated into the imaging device, or may be a constituent element of a signal processing device that is electrically connected in a wired or wireless manner to the imaging device. In FIG. 1, each of the image-forming optical system 102 and the relay optical system 103 is drawn as a single lens, but they may be an assembly of a plurality of lenses.

The light source 107 in the present embodiment is a laser light source that emits pulsed light of the ultraviolet region having two wavelength components. The light source 107 repeatedly emits short-pulse ultraviolet light rays in accordance with control signals that are input from the control circuit 108. These short-pulse ultraviolet light rays excite the target 101 (gas) within a detection target space, and cause the generation of Raman scattered light that accompanies wavelength shifts corresponding to gas molecules. At such time, distinctive Raman Stokes light is generated in the gas molecules that have shifted to the long wavelength side compared with the wavelength of the incident ultraviolet light rays (also called "excitation light").

The wavelength shift of the Raman Stokes light of the gas molecules is disclosed in Japanese Unexamined Patent Application Publication No. 2005-91343, and is known to have the numerical values given in Table below. In the present embodiment, a description is given of an example of the case where the wavelengths of laser pulsed light emitted from the light source 107 have been set to 355 nm and 266 nm. It should be noted that these wavelengths are examples, and other wavelengths may be used. Furthermore, the light source 107 may be configured so as to emit pulsed light having three or more wavelength components.

TABLE

| MOLE-CULE | RAMAN SHIFT ($cm^{-1}$) | RAMAN SCATTERING WAVELENGTH (nm) WHEN LASER WAVELENGTH IS 355 nm | RAMAN SCATTERING WAVELENGTH (nm) WHEN LASER WAVELENGTH IS 266 nm |
|---|---|---|---|
| $CO_2$ | 1286 | 372.0 | 275.4 |
| $CO_2$ | 1388 | 373.4 | 276.2 |
| $O_2$ | 1556 | 375.8 | 277.5 |
| CO | 2145 | 384.3 | 282.1 |
| $N_2$ | 2331 | 387.0 | 283.6 |
| $H_2S$ | 2611 | 391.3 | 285.9 |
| $CH_4$ | 2914 | 396.0 | 288.4 |
| $CH_4$ | 3020 | 397.6 | 289.2 |
| $NH_3$ | 3334 | 402.7 | 291.9 |
| $H_2O$ | 3652 | 407.9 | 294.6 |
| $H_2$ | 4160 | 416.5 | 299.1 |

The light emitted from the light source 107 in the present embodiment is in the ultraviolet wavelength band (approximately 10 nm to approximately 400 nm); however, it should be noted that the wavelength of the light from the light source 107 may be appropriately selected according to use. For example, as described in embodiment 3, in an imaging device that measures biological tissue, the near-infrared wavelength band (approximately 700 nm to approximately 2500 nm) may be used. In addition, it is also possible to use the visible light wavelength band (approximately 400 nm to approximately 700 nm), mid-infrared rays, far-infrared rays, or electromagnetic waves of the radio wave band such as terahertz waves or millimeter waves. In the present specification, not only visible light but also invisible light such as near-ultraviolet rays, near-infrared rays, and radio waves are referred to as "light" for convenience.

The imaging device of the present embodiment detects Raman Stokes light generated from gas molecules due to the irradiation of pulsed light, by means of the image sensor 106 via the optical system. At such time, detection is performed a plurality of times at high speed at different timings by means of highly time-resolved imaging. Thus, an image having a plurality of wavelength components superimposed thereon is acquired for each distance range of the target 101. Signals indicating an image for each of the distance ranges (sometimes referred to as an "image signal") are sent to the signal processing circuit 112 and processed thereby. The signal processing circuit 112 has a first signal processing unit 109 and a second signal processing unit 110. The first signal processing unit 109 generates a plurality of new image signals that are obtained by separating the image signals for each distance range into each wavelength component. In the present specification, this processing is sometimes referred to as "spectral separation processing". The second signal processing unit 110 generates three-dimensional image data from the image signals that have been separated for each wavelength component. In a certain aspect, the first signal processing unit 109 and the second signal processing unit 110 may be realized as separate modules within the signal processing circuit 112. The first signal processing unit 109 and the second signal processing unit 110 may be realized by one processor executing different image processing programs. Details of the processing performed by the signal processing circuit 112 are described later on.

Hereinafter, details of the constituent elements will be described.

The control circuit 108 may be an integrated circuit such as a central processing unit (CPU) or a microcomputer. The control circuit 108 executes a control program recorded in a memory that is not depicted, for example, to thereby perform control in the form of a lighting instruction for the light source 107, an imaging instruction for the image sensor 106, and a calculation instruction for the signal processing circuit 112, for example.

The signal processing circuit 112 is a circuit that processes the image signals that are output from the image sensor 106. The signal processing circuit 112 may be realized by a digital signal processor (DSP), a programmable logic device (PLD) such as a field-programmable gate array (FPGA), a combination of a central processing unit (CPU) and a computer program, or a combination of a graphics processing unit (GPU) and a computer program, for example. It should be noted that the control circuit 108 and the signal processing circuit 112 may be realized by means of one integrated circuit.

In the imaging device, the Raman Stokes light generated from the gas molecules is collected by the image-forming optical system 102, and formed into an image on an image formation surface. At such time, wavelength components produced by Rayleigh scattering or the like of pulsed light having two wavelengths that become noise are cut by the excitation light cut filter 111.

The encoding element 104 is arranged on the image formation surface of the image-forming optical system 102. The encoding element 104 is a mask having a spatial distribution of light transmittance, and has a plurality of regions having different light transmittance arrayed two-dimensionally. More specifically, there are a plurality of regions having a first light transmittance, and a plurality of regions having a second light transmittance that is lower than the first light transmittance. The encoding element 104 transmits the incident light with the intensity thereof being modulated in accordance with location. This process performed by the encoding element 104 is referred to as "encoding".

Figure 2B:
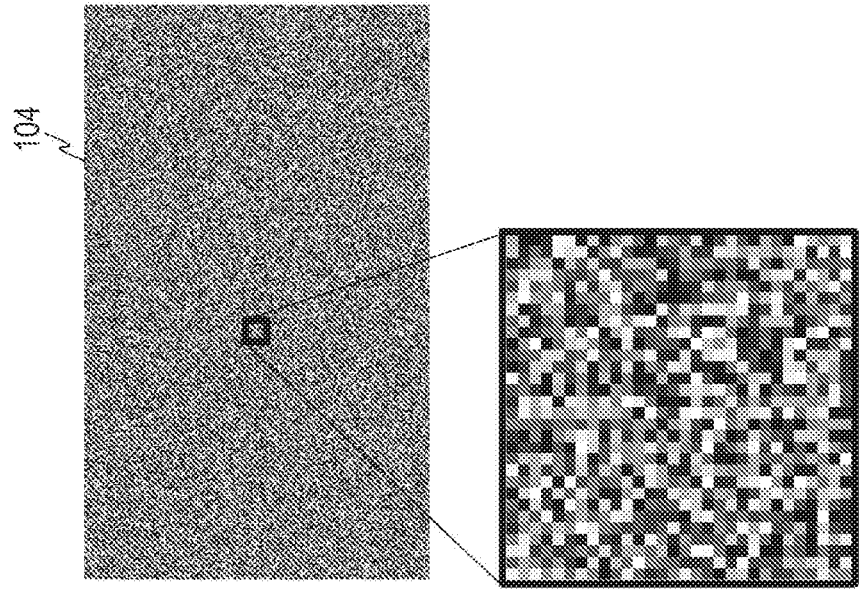
FIG. 2B is a drawing depicting another example of a two-dimensional distribution of light transmittance of the encoding element in embodiment 1 of the present disclosure.
Figure 2A:
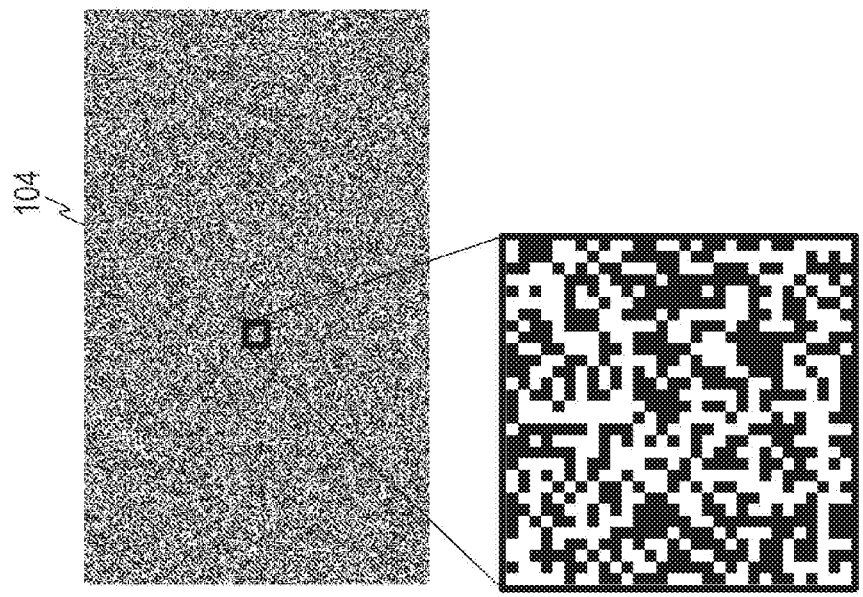
FIG. 2A is a drawing depicting an example of a two-dimensional distribution of light transmittance of an encoding element in embodiment 1 of the present disclosure.

FIG. 2A is a drawing depicting an example of a two-dimensional distribution of light transmittance of the encoding element 104. In FIG. 2A, the black portions represent regions through which light is mostly not transmitted (referred to as "light-blocking regions"), and the white portions represent regions through which light is transmitted (referred to as "light-transmitting regions"). In this example, the light transmittance of the light-transmitting regions is approximately 100%, and the light transmittance of the light-blocking regions is approximately 0%. The encoding element 104 is divided into a plurality of rectangular regions, and each rectangular region is a light-transmitting region or a light-blocking region. The two-dimensional distribution of the light-transmitting regions and the light-blocking regions in the encoding element 104 may be a random distribution or a quasi-random distribution, for example.

The thinking behind a random distribution and a quasi-random distribution is as follows. First, the rectangular regions in the encoding element 104 are deemed to be vector elements having values of 1 or 0, for example, in accordance with the light transmittance. In other words, a set of the rectangular regions arranged side-by-side in a row is deemed to be a multidimensional vector having values of 1 or 0. Consequently, the encoding element 104 is provided with a plurality of multidimensional vectors in the row direction. At such time, a random distribution means that any two multidimensional vectors are independent (not parallel). Furthermore, a quasi-random distribution means that non-independent configurations are included among some of the multidimensional vectors.

The encoding process performed by the encoding element 104 can be said to be a process for performing marking for distinguishing between images produced by light of each wavelength diffracted by the subsequent spectroscopic element 105. Provided that such marking is possible, the transmittance distribution may be set in an arbitrary manner. In the example depicted in FIG. 2A, the ratio between the number of black portions and the number of white portions is 1:1, but there is no restriction to such a ratio. For example, the distribution may be biased in one way, such as the number of white portions to the number of black portions being 1:9. The encoding element 104 schematically depicted in FIG. 1 has more (wider) light-transmitting regions than light-blocking regions.

FIG. 2B is a drawing depicting another example of a two-dimensional distribution of light transmittance of the encoding element 104. As depicted in FIG. 2B, the encoding element 104 may be a mask having a grayscale transmittance distribution. A grayscale transmittance distribution means a distribution that includes regions having an intermediate transmittance in which the transmittance is greater than 0% and less than 100%. Such an encoding element 104 has a plurality of rectangular regions having light transmittances that are different from the first and second light transmittances. Information regarding the transmittance distribution of the encoding element 104 is acquired in advance by means of design data or actual measured calibrations, and is used in signal processing that is described later on.

Reference will once again be made to FIG. 1. The spectroscopic element 105 in the present embodiment is an element that causes an incident light beam to be dispersed according to wavelength. The spectroscopic element 105 is configured from a combination of prisms made up of two materials. The two materials are selected from materials in which the refractive indexes for light of a specific wavelength are approximately the same and the Abbe numbers for light of that wavelength are different, for example, materials in which the Abbe numbers for light of that wavelength deviate. The specific wavelength may be set to a representative wavelength (dominant wavelength) within a desired spectral wavelength range, for example. The dominant wavelength may be a central wavelength in a measurement-target wavelength range or a wavelength that is considered to be important, for example. The Abbe number "deviating" here means that the difference between the Abbe numbers of the two materials is 10 or more. The difference between the Abbe numbers of the two materials may be 15 or more or may be 20 or more. The refractive indexes of the two materials being approximately the same means that the difference between the refractive indexes of the materials is 0.05 or less. The refractive indexes of the two materials being approximately the same may mean that the difference between the refractive indexes of the materials is 0.02 or less.

An Abbe number in the present specification is not restricted to an Abbe number relating to a Fraunhofer line wavelength that is generally used, and may be defined with respect to any wavelength. In the present disclosure, an Abbe number $\nu_b$ can be defined as in Math. 1 below with respect to arbitrary wavelengths $\lambda a$, $\lambda b$, and $\lambda c$ that satisfy $\lambda a < \lambda b < \lambda c$.

$$\nu_b = \frac{n_b - 1}{n_a - n_c} \qquad \text{(Math. 1)}$$

Here, na, nb, and nc each represent a refractive index in the wavelengths $\lambda a$, $\lambda b$, and $\lambda c$. $\lambda a$ and $\lambda c$ may be any wavelengths. $\lambda a$ and $\lambda c$ may be a wavelength near the start or end of the used wavelength band.

By making the surface onto which light rays are incident and the surface from which light rays are emitted substantially parallel in the spectroscopic element 105, it is possible to suppress the generation of coma aberration. Here, "substantially parallel" is not restricted to the case where the surfaces are strictly parallel, and includes the case where the angle formed by the two surfaces is 3° or less. This angle may be set to 1° or less or may be set to 0.5° or less. By using the spectroscopic element 105 such as that depicted in FIG. 1, an effect is obtained in that it is possible to reduce deterioration in the resolution of generated images for each wavelength band.

It should be noted that the spectroscopic element 105 does not necessarily have to be an element having two types of materials such as those described above joined together. For example, a general prism or diffraction optical element may be used.

Light encoded by the encoding element 104 is collected by the relay optical system 103 and input to the spectroscopic element 105. The spectroscopic element 105 diffracts light such that an optical image formed on an imaging surface of the image sensor 106 shifts in a direction corresponding to the image vertical direction (the vertical direction indicated in FIG. 1) in accordance with wavelength. The degree of that shift (sometimes referred to as the "diffraction amount") is determined according to the refractive indexes, the Abbe numbers, and the inclination angle of the connecting surfaces of the materials making up the spectroscopic element 105, and also the distance between the spectroscopic element 105 and the image sensor 106. In the case where the spectroscopic element 105 is a diffraction optical element, the diffraction amount can be adjusted by changing the pitch of the diffraction grating. In the present embodiment, the spectroscopic element 105 diffracts light in the direction corresponding to the image vertical direction, but may diffract light in the horizontal direction or another direction.

The amount of shift of the image on the imaging surface of the image sensor 106 due to the spectroscopic element 105 can be calculated in advance by a calculation based upon the design specifications or by means of actual measured calibrations. The spectral shift due to the spectroscopic element 105 is a continuous shift rather than a discrete shift for each measurement-target wavelength band. Meanwhile, in the signal processing circuit 112, as described later on, a spectral separation image is reconstructed for each wavelength band of a prescribed width. Therefore, strictly speaking, an image for each wavelength is shifted on the image sensor 106 even within the wavelength band for each image that is to be reconstructed. An image shift within the wavelength band may be corrected in order to improve the precision of the reconstruction of a spectral separation image. This correction may be performed by means of a computer calculation; however, when the effects of aberration in the optical system and mounting errors are also considered, the correction may be performed by means of actual measured calibrations. For example, it is possible for calibrations to be performed by arranging a white board in a prescribed location as a subject, and causing an image of the encoding element 104 to be formed on the image sensor 106 via a band pass filter for a desired wavelength band. The band pass filter may be switched for each band to acquire data of all desired bands; however, several bands may be selected and measured, and for other bands, calculations may be performed by interpolation of the measured data. According to this method, it is possible to calculate the spectral shift amount due to the spectroscopic element 105, and to also acquire transmittance information of the encoding element 104 for each wavelength band. Elements of a matrix H in Math. 2 described later on are determined on the basis of data of the calibrations calculated here.

A plurality of separated images having encoding information due to the encoding element 104 are formed on the image formation surface of the image sensor 106 while being shifted in the vertical direction for each wavelength, as a multiplex image in which the plurality of images overlap each other. The image sensor 106 captures this multiplex image. At such time, by performing high-speed time-resolved imaging, a plurality of images are acquired for each distance range of the target 101. Hereinafter, a configuration and operation of the image sensor 106 will be described.

The image sensor 106 has a plurality of photodetection cells (also referred to as "pixels" in the present specification) arrayed two-dimensionally on the imaging surface. The photodetection cells have a plurality of charge accumulation units (floating diffusion layers, for example).

FIG. 3 is a drawing depicting a schematic configuration example of one pixel 201 of the image sensor 106. It should be noted that FIG. 3 depicts the configuration of one pixel 201 in a schematic manner, and does not necessarily reflect the actual construction. The pixel 201 has: a photoelectric conversion unit (photodiode) 203 that performs photoelectric conversion; four floating diffusion layers (FD) 204 to 207 that accumulate signal charge; and a signal charge discharge unit (drain) 202 that discharges signal charge.

Photons that are incident on each pixel due to one emission of pulsed light are converted into signal electrons (signal charge) by the photodiode 203. The converted signal electrons are discharged to the drain 202 or divided into any of the floating diffusion layers 204 to 207 in accordance with control signals that are input from the control circuit 108.

The emission of pulsed light from the light source 107, the accumulation of signal charge to the first floating diffusion layer (FD1) 204, the second floating diffusion layer (FD2) 205, the third floating diffusion layer (FD3) 206, and the fourth floating diffusion layer (FD4) 207, and the discharge of signal charge to the drain 202 are repeatedly performed in this order. This repeated operation is high speed, and, for example, is able to be repeated several ten thousand times to several hundred million times within the time of one video frame (approximately 1/30 second, for example). Ultimately, the image sensor 106 generates and outputs four image signals that are based upon the signal charge accumulated in the four floating diffusion layers 204 to 207.

FIG. 4 is a flowchart depicting the flow of this operation. The control circuit 108, first, at a first time, causes the light source 107 to emit pulsed light that includes a plurality of wavelength components (step S101). At a subsequent second time, signal charge that is based upon light that is incident from a first portion of the target 101 is accumulated in the first floating diffusion layer 204 in the image sensor 106 (step S102). At a subsequent third time, signal charge that is based upon light that is incident from a second portion of the target 101 is accumulated in the second floating diffusion layer 205 in the image sensor 106 (step S103). Thereafter, signal charge is sequentially accumulated in the third floating diffusion layer 206 and the fourth floating diffusion layer 207 in a similar manner (steps S104 and S105). Next, signal charge is discharged to the drain 202 (step S106). Next, the control circuit 108 determines whether or not the number of times that the aforementioned signal accumulation cycle has been executed has reached a prescribed number of times (step S107). In the case where this determination is no, the steps S101 to S107 are repeated until a determination of yes is made. When a determination of yes is made in step S107, the control circuit 108 causes the image sensor 106 to generate and output an image signal that is based upon the signal charge accumulated in the floating diffusion layers (step S108).

Hereinafter, with reference to FIG. 5, a description will be given regarding the relationship between a timing at which pulsed light is emitted by the light source 107, timings at which Raman scattered light due to detection-target gas molecules reaches the image sensor 106, and timings at which light is received in the floating diffusion layers of the image sensor 106.

Figure 5:
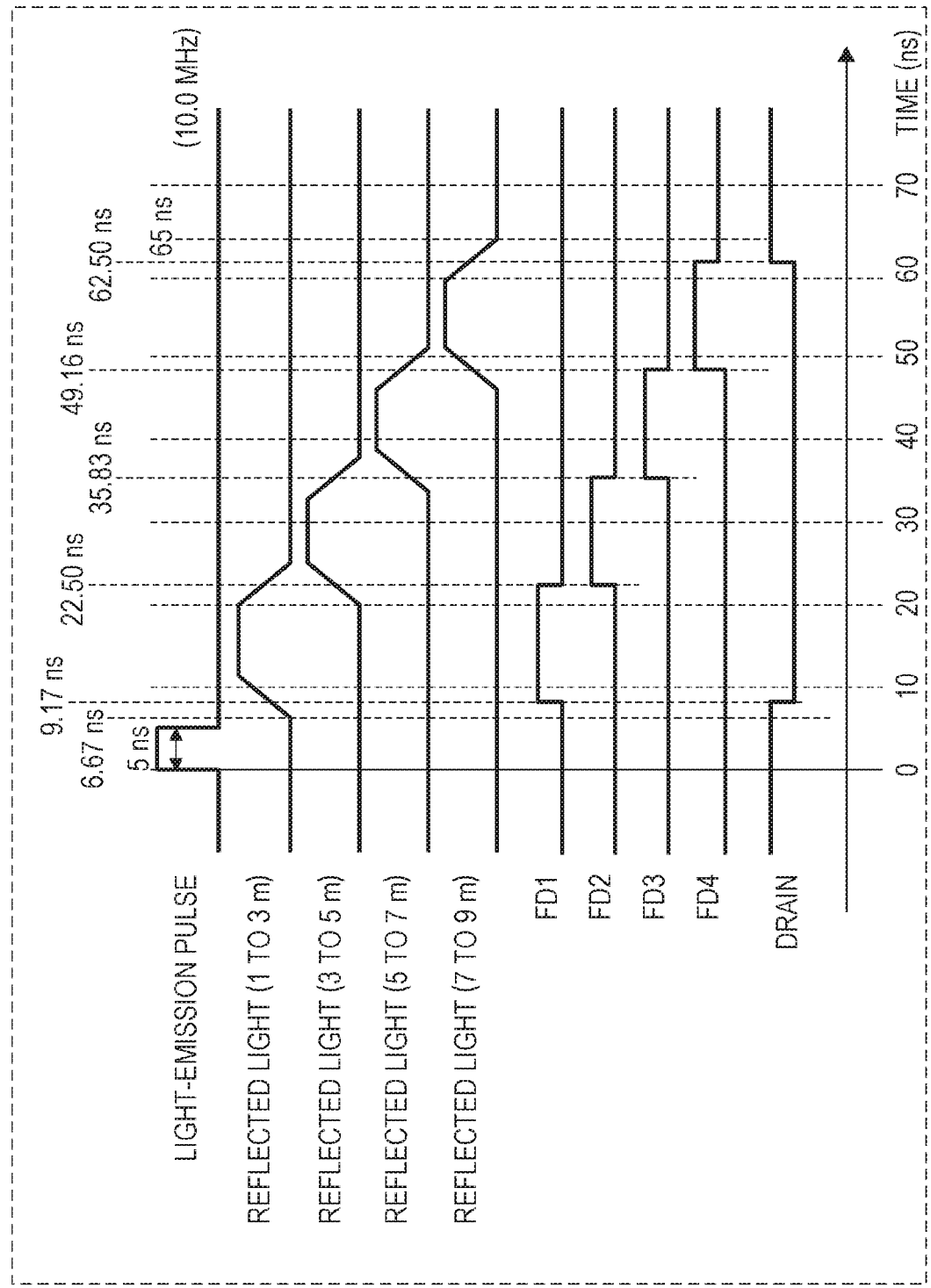
FIG. 5 is a drawing describing a relationship between a timing at which pulsed light is emitted by a light source, timings at which Raman scattered light due to detection-target gas molecules reaches the image sensor, and timings at which light is received in floating diffusion layers of the image sensor in embodiment 1 of the present disclosure.

FIG. 5 is a timing chart depicting a light-emission pulse, reflected light from each distance range portion of the target 101, control signals (referred to as "signal accumulation pulses") instructing signal charge to be accumulated in each of the floating diffusion layers (FD1 to FD4) 204 to 207, and a control signal (referred to as a "drain discharge pulse") instructing signal charge to be discharged to the drain 202.

In the present embodiment, the measurement distance range is taken as 9 m (18 m back and forth) at maximum, and four distance ranges are set at each 2 m. The speed of light is 300,000 km per second, and therefore the time required for light to travel back and forth over a maximum distance of 9 m is 60 ns. If the light-emission pulse width is set as 5 ns, the time required for one cycle is 65 ns, which is the time taken for a light component of the rear end of a light-emission pulse reflected from a location at a distance of 9 m to reach the imaging surface of the image sensor 106. In the present embodiment, in order to exclude the effect of Raman scattered light from afar due to the maximum distance range, a margin period is set as 35 ns with some allowance being taken, and the total time for one cycle is set as 100 ns. Consequently, the frequency of a light-emission pulse repeating cycle is the inverse thereof of 10 MHz.

The delay time from ultraviolet excitation light being irradiated onto gas molecules to Raman scattered light being generated is generally of the order of picoseconds (ps), and is an order that can be more or less ignored with the measurement distance ranges of the present embodiment. Thus, a description of this delay time has been omitted; however, the timing at which light is received by the image sensor 106 may be set with consideration being given to the time required for Raman scattering if necessary.

The light-emission wavelength, the light-emission pulse timing, and a drive timing for the image sensor 106 are appropriately set to optimal values in accordance with the distance range, the target gas, and the sensitivity of a light-receiving element. The numerical values used in the present embodiment are exemplary and do not restrict the scope of the patent claims in any way.

Ultraviolet excitation light, which is 10-MHz, 5-ns width pulsed light, is irradiated onto a gas such as carbon monoxide CO, hydrogen sulfide $H_2S$, or ammonia $NH_3$ in a target space. As a result, Raman scattered light of a wavelength corresponding to the gas molecules is generated. The wavelengths of the Raman scattered light for excitation light of 355 nm and 266 nm used in the present embodiment are as given in Table.

The light source 107 emits light-emission pulses in accordance with control signals that are input from the control circuit 108. In the example of FIG. 5, light is emitted at a timing of 0 ns, and the light is extinguished at a timing of 5 ns. At such time, in order to exclude signal charge caused by unnecessary Raman scattering generated at a close distance of less than 1 m outside of the measurement target range, the drain discharge pulse is set to ON. During this time, unnecessary signal charge generated by the photodiode 203 is discharged from the drain 202.

Raman scattered light that includes a plurality of wavelength components reaches the image sensor 106 being delayed according to distance as depicted in FIG. 5. This Raman scattered light is formed into a multiplex image that is encoded and diffracted in the vertical direction, and is converted into signal charge by the photodiode 203.

In principle, components due to unnecessary Raman scattered light from a close distance of less than 1 m and components due to Raman scattered light of a distance of 1 to 3 m include crosstalk proportionate to a time corresponding to a light-emission pulse width of 5 ns. Therefore, in the present embodiment, the reception of light starts from a timing at which the crosstalk assumes a median value. Specifically, the reception of light starts from a timing of 9.17 ns obtained by adding 2.5 ns, which is half of the light-emission pulse width, from a timing of 6.67 ns at which components of reflected light (1 to 3 m) start to reach the imaging surface of the image sensor 106.

The control circuit 108 sets the signal accumulation pulse for the first floating diffusion layer (FD1) 204 to ON at the same time as setting the drain discharge pulse to OFF at the timing of 9.17 ns depicted in FIG. 5. The signal accumulation pulse for the first floating diffusion layer 204 is then set to OFF at the timing of 22.50 ns, which is when the components of reflected light (1 to 3 m) attenuate and result in a 50% amount of light. Signal charge is thereby transferred and accumulated in the first floating diffusion layer 204. Similarly, the control circuit 108 sequentially sets signal accumulation pulses for the second to fourth floating diffusion layers (FD2 to FD4) 205 to 207 to ON at the timings depicted in FIG. 5. Time-resolved signal charge that includes crosstalk proportionate to the light-emission pulse width of 5 ns is thereby sequentially transferred and accumulated in the second to fourth floating diffusion layers 205 to 207. The control circuit 108 sets the drain discharge pulse to ON at the timing of 62.5 ns at which the signal accumulation pulse for the fourth floating diffusion layer 207 is set to OFF. Unnecessary signal charge due to Raman scattering generated from afar outside of the measurement target range is thereby discharged from the drain 202.

By repeating the above series of operations several ten thousand times to several hundred million times as required at the frequency of 10 MHz, signal charge of one frame of the image sensor 106 is accumulated. The number of times repeated is adjusted according to the light emission intensity of the light source 107 and the sensitivity of the image sensor 106. The Raman scattered light is weak, and therefore, by repeatedly performing this high-speed imaging synchronized with the laser excitation light a considerable number of times, it is possible to compensate for a lack of sensitivity.

In the present embodiment, the number of time resolution according to the plurality of floating diffusion layers is four; however, it should be noted that the number of time resolutions may be designed as a number other than four in accordance with the purpose.

Next, a signal read operation subsequent to signal accumulation in the image sensor 106 will be described with reference to FIG. 6.

Figure 6:
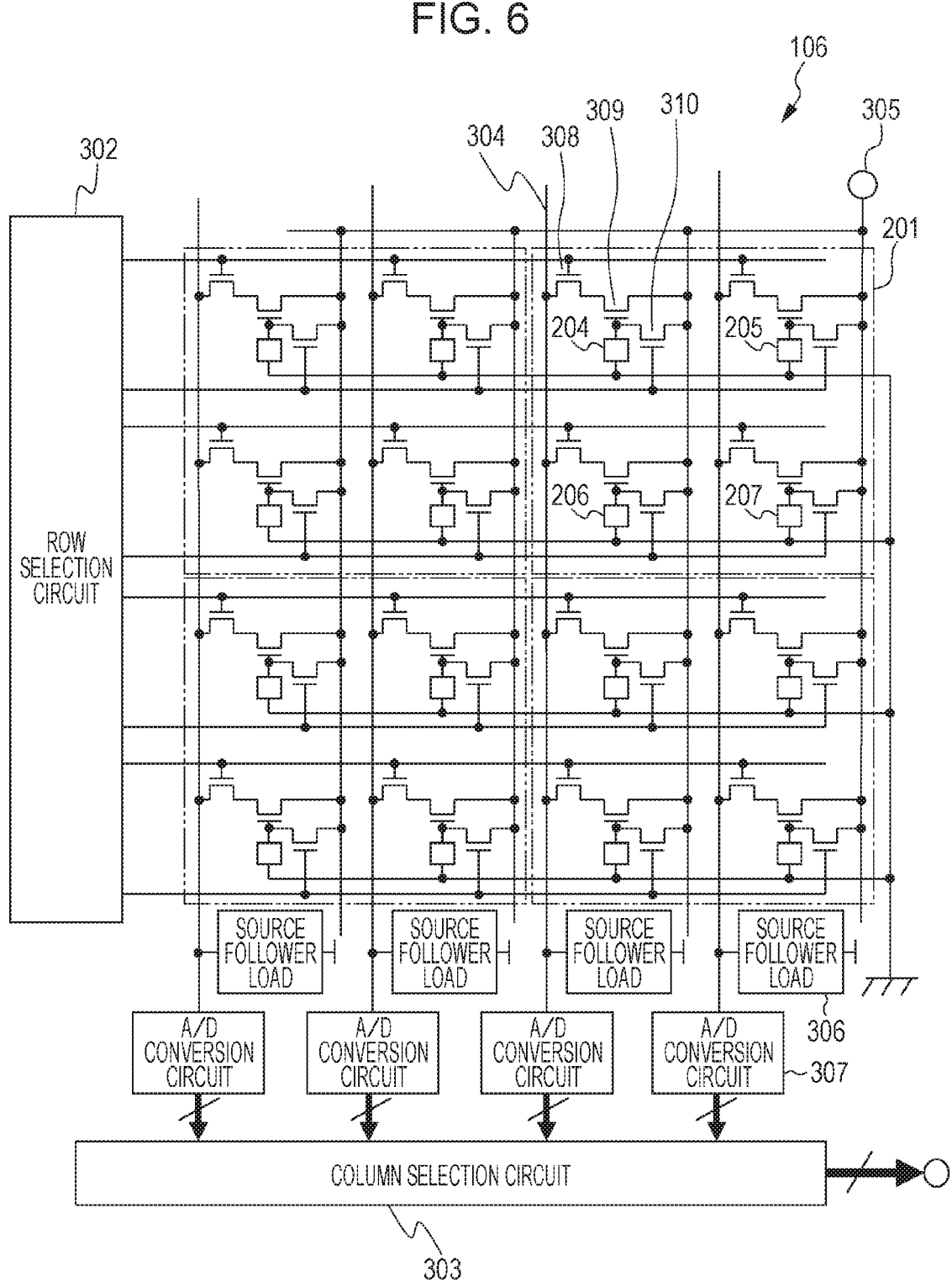
FIG. 6 is a drawing depicting an example of an overall configuration of the image sensor in embodiment 1 of the present disclosure.

FIG. 6 is a drawing depicting an example of the overall configuration of the image sensor 106. A region surrounded by a two-dot chain line border in FIG. 6 corresponds to one pixel 201. The pixel 201 includes four floating diffusion layers 204 to 207. Signals accumulated in the four floating diffusion layers 204 to 207 are treated as if they were signals of four pixels of a general CMOS image sensor, and are output from the image sensor 106.

Each pixel 201 has four signal detection circuits. Each signal detection circuit includes a source follower transistor (amplification transistor) 309, an FD signal-reading transistor (row selection transistor) 308, and a reset transistor 310. In this example, the reset transistor 310 corresponds to the drain 202 depicted in FIG. 3, and a pulse that is input to the gate of the reset transistor 310 corresponds to the aforementioned drain discharge pulse. The transistors are field effect transistors formed on a semiconductor substrate, for example, but are not restricted thereto. As depicted, one of the input terminal and output terminal of the source follower transistor 309 (typically the source) and one of the input terminal and output terminal of the FD signal-reading transistor 308 (typically the drain) are connected. The control terminal (gate) of the source follower transistor 309 is connected to the photodiode 203. Signal charge (positive holes or electrons) generated by the photodiode 203 is accumulated in the floating diffusion layers 204 to 207, which are charge accumulation nodes between the photodiode 203 and the source follower transistor 309.

Although not detected in FIG. 6, the four floating diffusion layers 204 to 207 are connected to the photodiode 203, and a switch is provided between the photodiode 203 and the floating diffusion layers. This switch switches the conduction state between the photodiode 203 and the floating diffusion layers 204 to 207 in accordance with a signal accumulation pulse from the control circuit 108. The starting and stopping of the accumulation of signals to the floating diffusion layers 204 to 207 is controlled thereby.

Signal charge accumulated in the floating diffusion layers 204 to 207 by the abovementioned repeated operation is read out due to the gate of the FD signal-reading transistor 308 being set to ON by a row selection circuit 302. At such time, current that flows from a source follower power source 305 to the source follower transistor 309 and a source follower load 306 is amplified in accordance with the signal potential of the floating diffusion layers 204 to 207. An analog signal produced by this current that is read out from a vertical signal line 304 is converted into digital signal data by an analog-digital (AD) conversion circuit 307 that is connected to each column. This digital signal data is read out for each column by a column selection circuit 303, and is output from the image sensor 106. The row selection circuit 302 and the column selection circuit 303, after having performed reading for one row, perform reading for the next row, and, similarly thereafter, read out signal charge information of the floating diffusion layers for all of the rows. After all of the signal charge has been read out, the control circuit 108 resets all of the floating diffusion layers by setting the gate of the reset transistor 310 to ON. Imaging for one frame is thereby completed. Similarly thereafter, by repeating high-speed imaging for frames, imaging for a series of frames by the image sensor 106 is concluded.

In the present embodiment, an example of a CMOS-type image sensor 106 has been described; however, the image sensor may be a CCD type, a single photon counting-type element, or an amplification-type image sensor (EMCCD, ICCD).

Next, a description will be given regarding processing (spectral separation processing) for separating, into each wavelength component, each of four time-resolved images output from the image sensor 106. This processing is performed by the first signal processing unit 109 in the signal processing circuit 112 depicted in FIG. 1.

Figure 7:
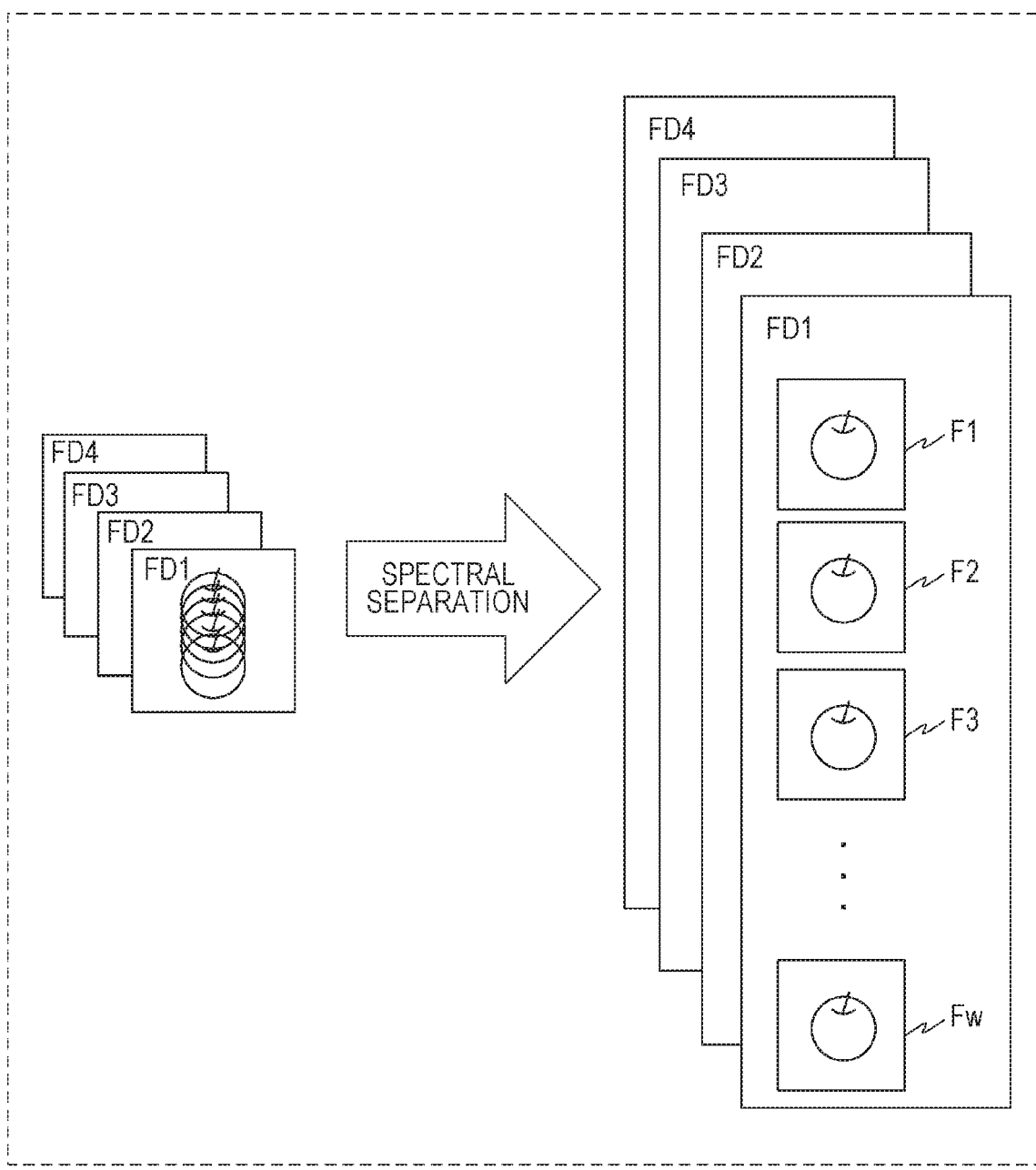
FIG. 7 is a conceptual diagram depicting an impression of spectral separation processing in embodiment 1 of the present disclosure.

FIG. 7 is a conceptual diagram depicting an impression of this spectral separation processing. Images of apples are used in FIG. 7 to convey this impression, but this is merely for convenience in order to describe a multiplex image. The first signal processing unit 109 separates a multiplex image that is overlapped while being shifted in the vertical direction with respect to each wavelength, into a plurality of images of each wavelength in accordance with the following procedure. This image separation is performed for each of the four images that are based upon the signal charge accumulated in the floating diffusion layers 204 to 207. More specifically, for each of the four images, address shifts in the vertical direction in the wavelength component images are corrected, and w number of images F1 to Fw having the same address and not having any overlapping due to wavelength are generated. The number w of images generated here may be any number equal to or greater than 2. For example, a number that is equal to or greater than 4 and equal to or less than 100 may be used.

The desired data is the spectral separation images F1 to Fw, and that data is represented as f. The number of spectral bands (number of bands) is w, and therefore f is data for which the image data f1, f2 ... fw of each band is integrated. If the number of pixels in the x direction of the image data to be obtained is taken as n and the number of pixels in the y direction is taken as m, each of the image data f1, f2 ... fw is a collection of two-dimensional data of n×m pixels.

Consequently, the data f is three-dimensional of n×m×w number of elements. When a spectroscopic element P causes a spectral image to shift one pixel at a time in the y direction for each spectral band to be obtained, the number of elements of data g of a captured image G that is acquired is n×(m+w−1). The data g in the present embodiment can be represented by Math. 2 below.

$$g = Hf = H \begin{bmatrix} f_1 \\ f_2 \\ \vdots \\ f_w \end{bmatrix}$$ (Math. 2)

Here, f1, f2 . . . fw is data having n×m elements, and therefore, strictly speaking, a right-side vector is a one-dimensional vector of n×m×w rows and one column. A vector g is represented and calculated by being converted into a one-dimensional vector of n×(m+w−1) rows by one column. The matrix H represents a conversion in which the vector f is intensity-modulated by means of encoding, and the components f1, f2 . . . fw are shifted one pixel at a time in the y direction and added. Consequently, H is a matrix of n(m+w−1) rows and n×m×w columns.

Here, it is assumed that images of the wavelength bands are shifted one pixel at a time, and therefore the number of elements of g is taken as n×(m+w−1); however, it is not absolutely necessary to shift the images one pixel at a time. The number of pixels by which shifting is performed may be two or more pixels. The number of pixels by which shifting is performed depends on the way which spectral bands and the number of spectral bands in a spectral separation image F to be reconstructed have been set. The number of elements of g changes according to the number of pixels by which shifting is performed. Furthermore, the spectral direction is also not restricted to the y direction, and shifting may be performed in the x direction. To generalize, in the case where an image is shifted ky pixels at a time in the y direction and kx pixels at a time in the x direction with ky and kx being arbitrary natural numbers, the number of elements of data g becomes {n+kx·(w−1)}×{m+ky·(w−1)}.

Then, if the vector g and the matrix H are applied, it is seemingly possible to calculate f by solving the inverse problem of Math. 2. However, the number of elements n×m×w of the data f to be obtained is greater than the number of elements n(m+w−1) of the acquired data g, and therefore this problem is an ill-posed problem and cannot be solved as it is. Thus, the signal processing circuit 112 of the present embodiment uses the redundancy of the images included in the data f, and obtains a solution using the compressed sensing method. Specifically, the data f to be obtained is estimated by solving the equation of Math. 3 below.

$$f' = \underset{f}{\mathrm{argmin}}\{\|g - Hf\|_{l_2} + \tau \Phi(f)\}$$ (Math. 3)

Here, f' represents the data for f that is estimated. The first term within the brackets of the equation above represents the amount of deviation between an estimation result Hf and the acquired data g, what is referred to as the residual term. The square sum serves as the residual term here, but an absolute value, the square root of the square sum, or the like may serve as the residual term. The second term within the brackets is a regularization term (or a stabilization term) that is described later on. Math. 3 means that f is obtained with the sum of the first term and the second term being minimized. The signal processing circuit 112 is able to converge the solution by means of a recursive iterative operation, and calculate the final solution f'.

The first term within the brackets of Math. 3 means a calculation that obtains the square sum of the difference between the acquired data g and Hf, for which f of the estimation process is system-converted according to the matrix H. φ(f) of the second term is a constraint in the regularization for f, and is a function that reflects sparse information of the estimated data. As an operation, there is an effect in that the estimated data is made smooth or stable. The regularization term, for example, may be represented by a discrete cosine transform (DCT), wavelet transform, Fourier transform, total variation (TV), or the like of f. For example, in the case where total variation is used, it is possible to obtain stable inferred data in which the effect of noise of the observed data g is suppressed. The sparsity of the measurement target in the space of respective regularization terms is different depending on the texture of the measurement target. The regularization term with which the texture of the measurement target becomes sparser in the space of the regularization term may be selected. Alternatively, a plurality of regularization terms may be included in the calculation. τ is a weighting coefficient, and the amount of redundant data reduced increases (the compression ratio increases) as this value increases, and the convergence to a solution weakens as this value decreases. The weighting coefficient is set to an appropriate value with which f converges to an extent and over-compression does not occur.

A calculation example using the compressed sensing indicated in Math. 3 has been given here, but it should be noted that a solution may be found using another method. For example, it is possible to use another statistical method such as a maximum likelihood estimation method, a Bayesian inference method, or the like. Furthermore, the number of spectral separation images F1 to Fw is arbitrary, and the wavelength bands may also be arbitrarily set.

Next, 3D image generation processing by the second signal processing unit 110 depicted in FIG. 1 will be described.

Figure 8:
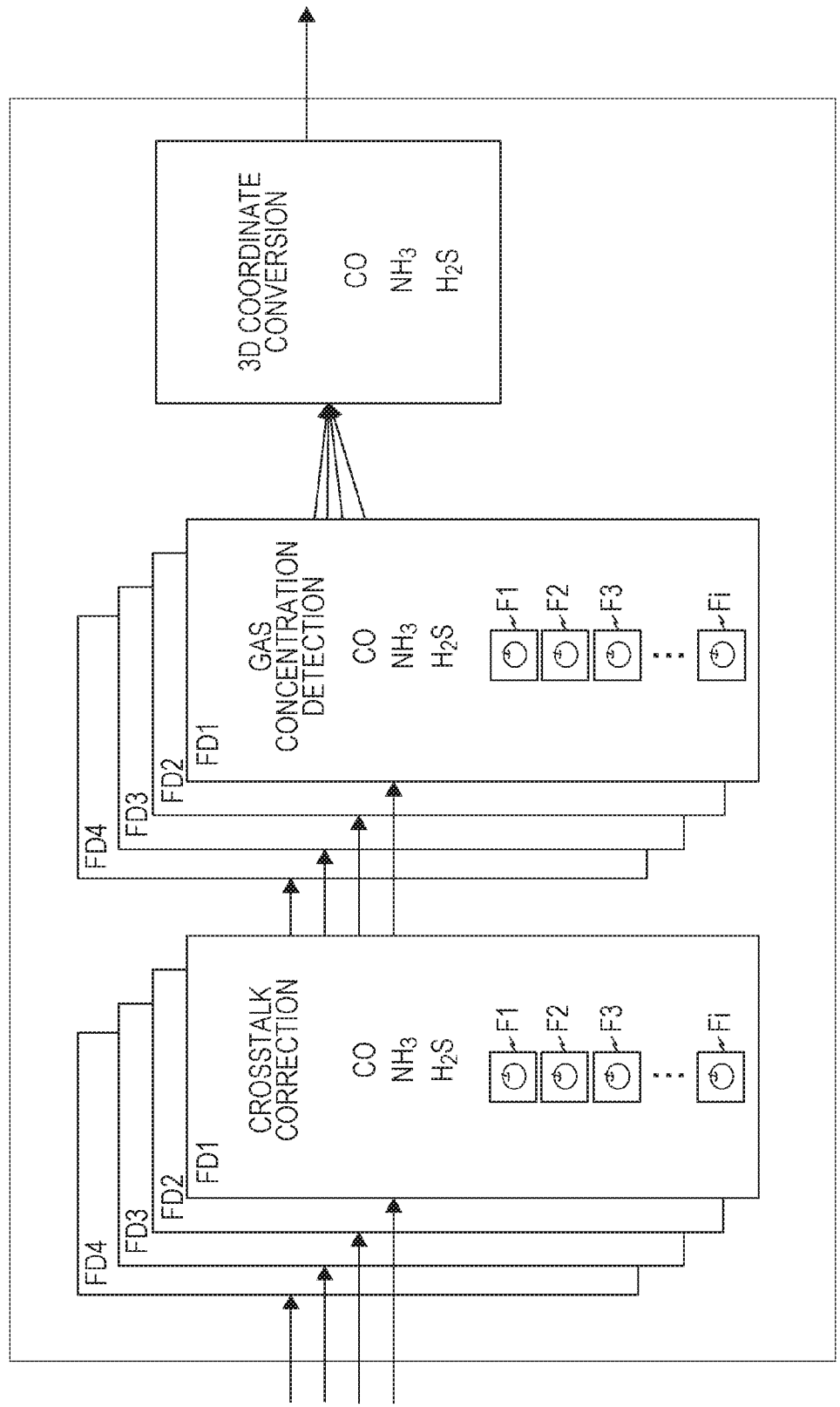
FIG. 8 is a drawing depicting an overview of 3D image generation processing by a second signal processing unit in embodiment 1 of the present disclosure.

FIG. 8 is a drawing depicting an overview of the 3D image generation processing by the second signal processing unit 110. Four two-dimensional (2D) images FD1 (1 to 3 m), FD2 (3 to 5 m), FD3 (5 to 7 m), and FD4 (7 to 9 m) for each distance range are obtained by means of the aforementioned time-resolved imaging. The second signal processing unit 110 appropriately applies a spatial high-pass enhancement filter to level changes for same pixel addresses between images in these 2D images. Thus, the effect of crosstalk generated due to the light-emission pulse time of the pulse light source 107 having a finite length (5 ns, for example), in other words, the effect that changes in pixel values of the same address decrease, is corrected.

Next, the type of gas is identified on the basis of a plurality of images for each wavelength band generated by the first signal processing unit 109. For example, in the case where excitation light having two wavelengths of 355 nm and 266 nm is used to detect three types of gas (CO, $NH_3$, and $H_2S$), according to the aforementioned Table, attention may be paid to the components of the wavelengths of 282.1 nm, 285.9 nm, 289.2 nm, 384.3 nm, 391.3 nm, and 402.7 nm. In the case where the first signal processing unit 109 has generated a spectral separation image for each component of these wavelengths, by detecting the wavelength at which the intensity peaks, it is possible to identify the type of the gas, and it is possible to detect the concentration from the intensity level of the light of that peak wavelength.

Since the imaging-target space in the present embodiment is a light-transmitting body, the XY coordinates (pixel addresses) of the four images of FD1 to FD4 directly represent data with respect to the front direction of the horizontal direction and the vertical direction from the location of the imaging device (camera). Meanwhile, FD1 to FD4 directly correspond to distance ranges from the imaging device. Therefore, by performing a simple address conversion on the pixels of FD1 to FD4, it is possible for three-dimensional XYZ coordinates to be calculated. A 3D spatial concentration distribution image of a desired gas is thereby obtained.

Embodiment 2

Figure 9:
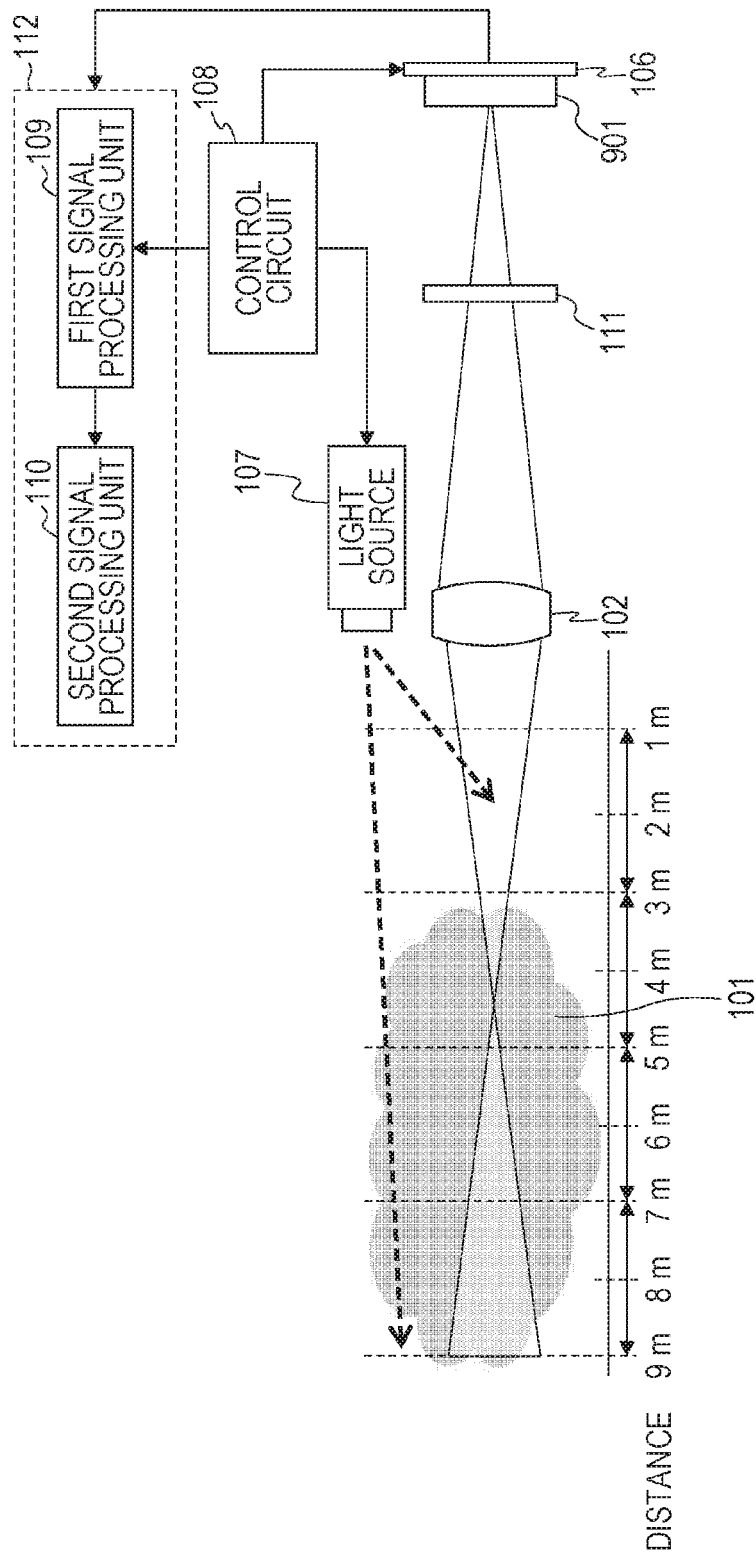
FIG. 9 is a drawing depicting a configuration of embodiment 2 of the present disclosure.

Next, embodiment 2 of the present disclosure will be described. Similar to embodiment 1, the purpose of the imaging device in the present embodiment is to detect the type and concentration of a gas, and it is possible to convert a spatial distribution of the concentration of a gas into a 3D image. The difference with embodiment 1 is that, as depicted in FIG. 9, an encoding spectroscopic element 901 in which an encoding element and a spectroscopic element are integrated is arranged directly in front of a time-resolved image sensor 106, and the relay optical system has therefore been eliminated. Hereinafter, the present embodiment will be described with reference to FIGS. 9 and 10 focusing on the difference with embodiment 1.

The operation up to Raman scattered light being input to the excitation light cut filter 111 is the same as in embodiment 1, and therefore a description thereof has been omitted.

FIG. 10 is a drawing schematically depicting a configuration of the encoding spectroscopic element 901. As depicted in (a) of FIG. 10, the encoding spectroscopic element 901 has a plurality of regions arrayed two-dimensionally. The regions are formed of a transparent member, and have individually set spectral transmittances. Here, "spectral transmittance" means the wavelength distribution of light transmittance. Spectral transmittance is represented by the function $T(\lambda)$, with the wavelength of incident light as $\lambda$. Spectral transmittance $T(\lambda)$ may take a value that is equal to or greater than 0 and equal to or less than 1. In (a) of FIG. 10, 48 rectangular regions arrayed in six rows by eight columns are exemplified; however, in actual use, many more regions than this may be provided. The number thereof may be of the same level as the number of pixels (several hundred thousand to several ten million, for example) of the image sensor 106, for example. In a certain example, the encoding spectroscopic element 901 may be arranged immediately above an image sensor, and each region may be arranged so as to correspond to (oppose) one pixel of the image sensor.

In (b) of FIG. 10, an example of the spatial distribution of the transmittance of light of each of a plurality of wavelengths W1, W2 . . . Wi of a detection target is depicted. In this drawing, differences in the shade of each region (cell) represents differences in transmittance. The transmittance increases with lighter regions, and the transmittance decreases with darker regions. As depicted in (b) of FIG. 10, the spatial distribution of light transmittance is different depending on the wavelength band.

In (c1) and (c2) of FIG. 10, examples of the spectral transmittance in two regions A1 and A2 in the encoding spectroscopic element 901 are depicted. The spectral transmittance in the region A1 and the spectral transmittance in the region A2 are different. In this way, the spectral transmittance in the encoding spectroscopic element 901 is different depending on the region. However, it is not absolutely necessary for the spectral transmittances of all of the regions to be different. The spectral transmittances of at least some (two or more) regions from among the plurality of regions in the encoding spectroscopic element 901 may be different from each other. In a certain example, the number of patterns of the spectral transmittances of a plurality of regions included in the encoding spectroscopic element 901 may be the same as or more than the number i of wavelength bands included in the target wavelength bands. Typically, the encoding spectroscopic element 901 is designed such that the spectral transmittance is different in half of the regions or more.

Figure 11A:
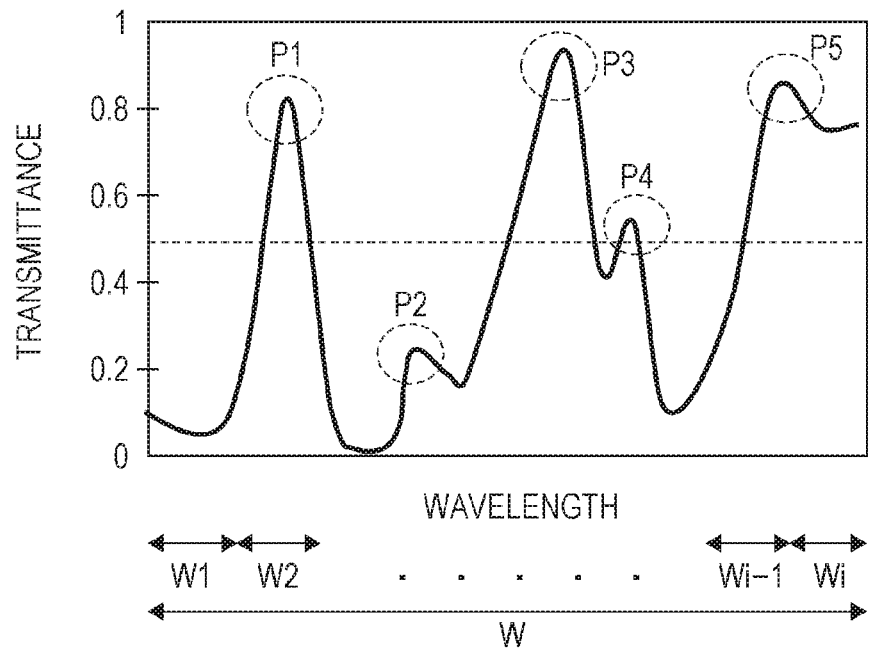
FIG. 11A is a drawing for describing spectral transmittance characteristics in a certain region of the encoding spectroscopic element in embodiment 2 of the present disclosure.

FIG. 11A is a drawing for describing spectral transmittance characteristics in a certain region of the encoding spectroscopic element 901. The spectral transmittance in this example has a plurality of maximum values P1 to P5 and a plurality of minimum values in relation to the wavelengths within the target wavelength bands W. In this example, the maximum values for spectral transmittance are present in the wavelength bands W2, Wi−1, and the like. In this way, in the present embodiment, the spectral transmittance of each region has a maximum value in a plurality of (at least two) wavelength bands within the plurality of wavelength bands W1 to Wi.

The light transmittance of each region is different depending on the wavelength, and therefore, from within incident light, the encoding spectroscopic element 901 transmits a large number of the components of a certain wavelength band, and does not transmit the components of other wavelength bands to the same extent. For example, transmittance is greater than 0.5 (50%) for the light of k number (k being an integer satisfying $2 \leq k < i$) of wavelength bands from among i number of wavelength bands, and transmittance is less than 0.5 (50%) for the light of the remaining i−k number of wavelength bands. In the case where the incident light is white light that includes all of the wavelength components of visible light equally, the encoding spectroscopic element 901 modulates, for each region, the incident light to light having a plurality of discrete intensity peaks in relation to wavelength, and superimposes and outputs this multi-wavelength light.

Figure 11B:
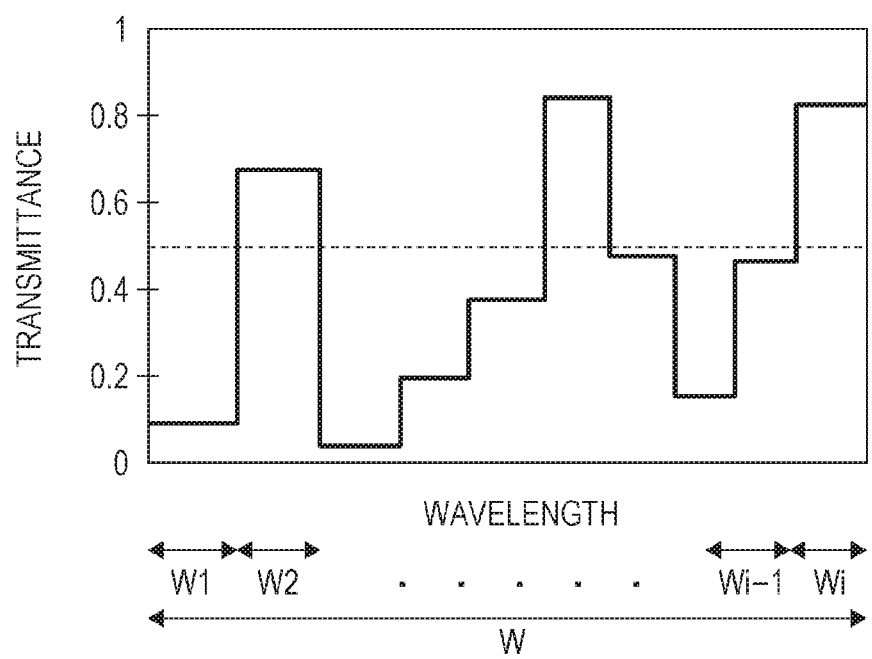
FIG. 11B is a drawing depicting results of averaging the spectral transmittance depicted in FIG. 11A in each wavelength band.

FIG. 11B, as an example, is a drawing depicting results of averaging the spectral transmittance depicted in FIG. 11A in each wavelength band W1, W2 . . . Wi. The averaged transmittance is obtained by the spectral transmittance $T(\lambda)$ being integrated for each wavelength band and divided by the width (bandwidth) of that wavelength band. In the present specification, a transmittance value obtained by averaging for each wavelength band in this way is referred to as the transmittance in the wavelength band in question. In this example, the transmittance increases in a prominent manner in the three wavelength bands having the maximum values P1, P3, and P5. In particular, the transmittance exceeds 0.8 (80%) in the two wavelength bands having the maximum values P3 and P5.

The wavelength-direction resolution of the spectral transmittance of each region may be set to the order of the width (bandwidth) of a desired wavelength band. In other words, from among a wavelength range that includes one maximum value (peak) in a spectral transmittance curve, the width of a range that takes a value that is equal to or greater than the average value for the minimum value closest to said maximum value and said maximum value may be set to the order of the width (bandwidth) of a desired wavelength band. In such a case, if the spectral transmittance is resolved to frequency components using a Fourier transform or the like, the values of the frequency components corresponding to that wavelength band increase in a relative manner.

The encoding spectroscopic element 901, typically, as depicted in (a) of FIG. 10, is divided into a plurality of regions (cells) that are partitioned in a grid pattern. These cells have mutually different spectral transmittance characteristics. The wavelength distribution and spatial distribution of the light transmittance of each region in the encoding spectroscopic element 901 may be the aforementioned random distribution or quasi-random distribution, for example.

In the case where the encoding spectroscopic element 901 is arranged near to or immediately above the image sensor 106, the gaps (cell pitches) between the plurality of regions in the encoding spectroscopic element 901 may substantially match the pixel pitches of the image sensor 106. If so, the resolution of an optical image that is emitted from the encoding spectroscopic element 901 and encoded substantially matches the pixel resolution. By making light that has passed through the cells be incident on only one corresponding pixel, calculations that are described later can be facilitated. In the case where the encoding spectroscopic element 901 is arranged away from the image sensor 106, the cell pitch may be reduced according to that distance.

In the example depicted in FIG. 10, a grayscale transmittance distribution in which the transmittance of each region may take any value equal to or greater than 0 and equal to or less than 1 is assumed. However, it is not absolutely necessary to implement a grayscale transmittance distribution. For example, a binary scale transmittance distribution in which the transmittance of each region may take either of the values of approximately 0 or approximately 1 may be adopted. In a binary scale transmittance distribution, each region transmits the majority of the light of at least two wavelength bands from among a plurality of wavelength bands included in the target wavelength bands, and does not transmit (blocks) the majority of the light of the remaining wavelength bands. Here, the "majority" refers to approximately 80% or more.

Some cells (half, for example) from among all of the cells may be replaced with transparent regions. Such transparent regions transmit light of all of the wavelength bands W1 to Wi included in the target wavelength bands, at a high transmittance of the same level (0.8 or more, for example). In such a configuration, a plurality of the transparent regions may be arranged in a checkered form, for example. In other words, regions having different light transmittance due to wavelength and transparent regions may be arrayed in an alternating manner in two array directions (the horizontal direction and the vertical direction in (a) of FIG. 10) for the plurality of regions in the encoding spectroscopic element 901.

The encoding spectroscopic element 901 may be configured using at least one selected from the group consisting of a multilayer film, an organic material, a diffraction grating structure, and a microstructure including a metal. In the case where a multilayer film is used, for example, a dielectric multilayer film or a multilayer film including a metal layer may be used. In such a case, forming is carried out such that at least one selected from the group consisting of the thickness, material, and layering order of the multilayer films is different for each cell. It is thereby possible to realize spectral characteristics that are different depending on the cell. By using a multilayer film, it is possible to realize sharp rises and falls in spectral transmittance. A configuration in which an organic material is used may be realized by making the contained pigment or dye different depending on the cell, and by layering different types of materials. A configuration in which a diffraction grating structure is used may be realized by providing a diffraction structure having diffraction pitches or depths that are different for each cell. In the case where a microstructure including a metal layer is used, construction may be carried out using diffraction due to the plasmon effect.

According to the present embodiment, images having different encoding information for each wavelength band are formed overlapping each other as a multiplex image on the image formation surface of the image sensor 106. Different from embodiment 1, a spectroscopic element such as a prism is not used, and therefore there is no shift in the spatial direction of the images. It is thereby possible to maintain a high spatial resolution even with a multiplex image.

The time-resolved imaging operation performed by the image sensor 106 is the same as in embodiment 1, and therefore a description thereof has been omitted. Furthermore, there is no difference with embodiment 1 also with respect to the signal processing apart from the acquisition of a spectral multiplex image in which there is no spatial shift. Apart the processing for performing vertical-direction address correction, it is possible for a spectral separation image and a 3D image to be generated by means of the same processing as in embodiment 1. Thus, a description of the signal processing has been omitted.

In the present embodiment, it is possible to omit the relay optical system by using an encoding spectroscopic element. Therefore, compared with the configuration of embodiment 1, it is possible to realize the same functions with a small device.

Embodiment 3

For an imaging device of embodiment 3, a light scattering body such as a living body is a detection target. Molecules to be detected can be identified, and the concentration distribution thereof can be reconstructed as a 3D image. The imaging device of the present embodiment detects the concentration distribution of oxidized hemoglobin and deoxidized hemoglobin of blood within the brain, and time changes thereof. Near-infrared light of 700 to 900 nm, known as an optical tissue window in which absorption is relatively difficult with respect to both water and hemoglobin, may be used for a living body. Therefore, near-infrared light of this wavelength band is mainly used in the present embodiment.

Figure 12:
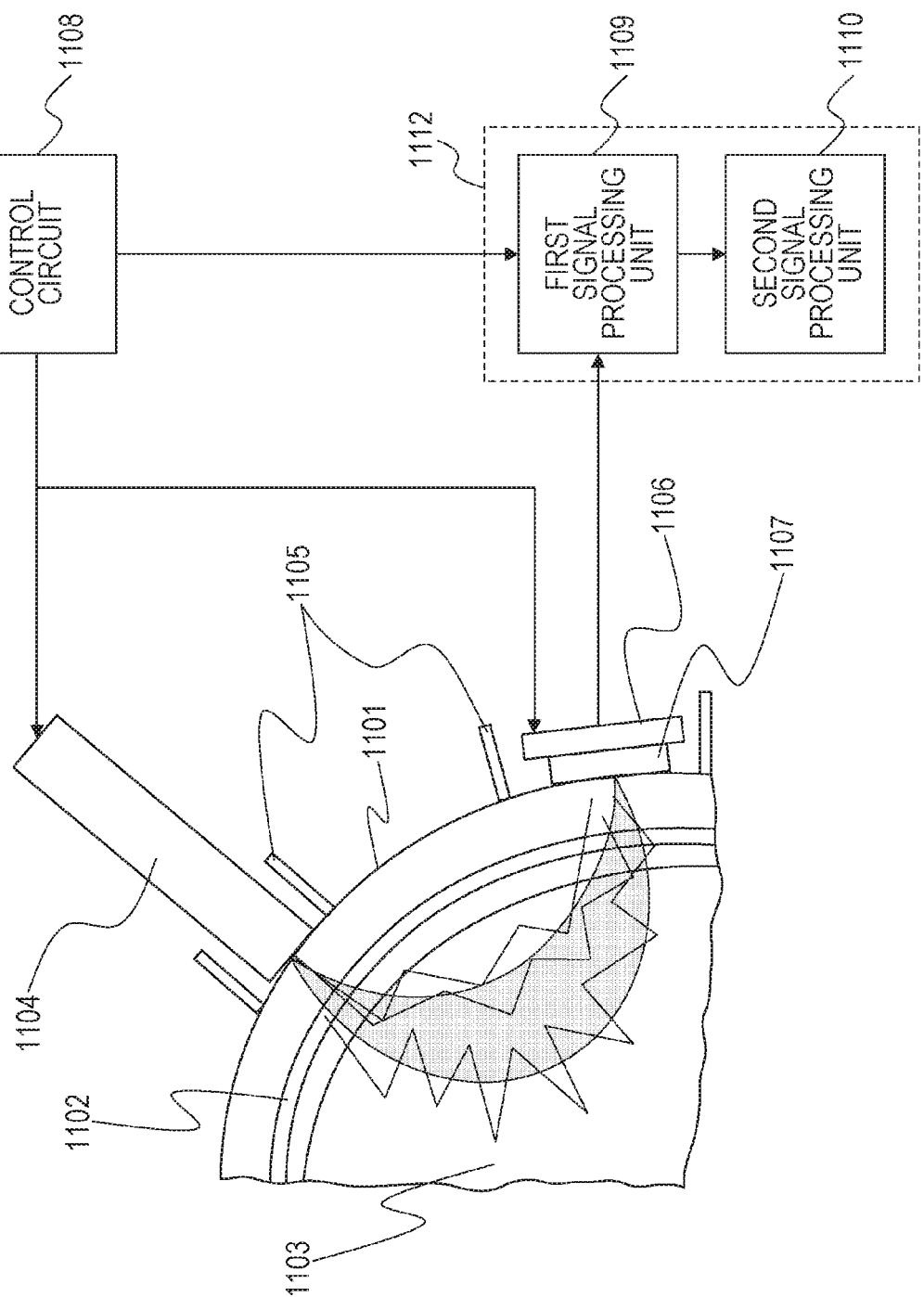
FIG. 12 is a drawing depicting a configuration of an imaging device in embodiment 3 of the present disclosure.

FIG. 12 is drawing depicting a schematic configuration of the imaging device of the present embodiment. The imaging device is provided with a near-infrared laser pulse light source 1104, an encoding spectroscopic element 1107, an image sensor 1106, a control circuit 1108, and a signal processing circuit 1112.

The near-infrared laser pulse light source 1104 irradiates a near infrared ray having broad spectral characteristics of 700 to 900 nm toward brain tissue 1103, which is the detection target. This irradiation is repeatedly performed in short pulses in accordance with control signals from the control circuit 1108.

In the present embodiment, loss due to reflection by the head surface 1101 is reduced, and near-infrared light is efficiently guided into the brain, and therefore the light source 1104 may be used in close contact with the head surface 1101. Furthermore, reflection may be reduced using a gel sheet, a cream, or the like. In the example depicted in FIG. 12, light-blocking plates 1105 are used in order to cut leakage light from skin.

A portion of the irradiated short-pulse infrared light rays passes through the cranium 1102, is repeatedly absorbed and elastically scattered within the brain tissue 1103, and propagates while attenuating. A portion thereof once again passes through the cranium 1102, passes through the head surface 1101, reaches a light-receiving surface of the image sensor 1106 via the encoding spectroscopic element 1107, and photoelectric conversion is performed.

One set of the light source 1104, the encoding spectroscopic element 1107, and the image sensor 1106 is drawn in FIG. 12 for simplicity; however, it should be noted that, in practice, a system may be implemented including a plurality of sets of the light source 1104, the encoding spectroscopic element 1107, and the image sensor 1106. A plurality of sets of the light source 1104, the encoding spectroscopic element 1107, and the image sensor 1106 may, for example, be arranged two-dimensionally at equal intervals (3 cm, for example). In the case where a plurality of sets of the light source 1104 and the image sensor 1106 are used, a measure such as the high-speed time-divided irradiation of a laser may be implemented in order to suppress crosstalk among light sources.

Hereinafter, an example in which one set of the light source 1104 and the image sensor 1106 is used will be described in detail.

The same encoding spectroscopic element as in embodiment 2 can be used for the encoding spectroscopic element 1107. Therefore, a detailed description of the encoding spectroscopic element 1107 has been omitted.

In the present embodiment, different from embodiment 1 and embodiment 2, the wavelength distribution of the light emitted from the light source 1104 is broad. In addition, since there is no image-forming optical system, the encoding spectroscopic element 1107 is positioned immediately in front of the image sensor 1106.

Images having different encoding information for each wavelength band are formed overlapping each other as a multiplex image on the light-receiving surface of the image sensor 1106. In the present embodiment, a spectroscopic element such as a prism is not used, and therefore there is no shift in the spatial direction of the images. It is thereby possible to maintain a high spatial resolution even with a multiplex image.

Figure 13:
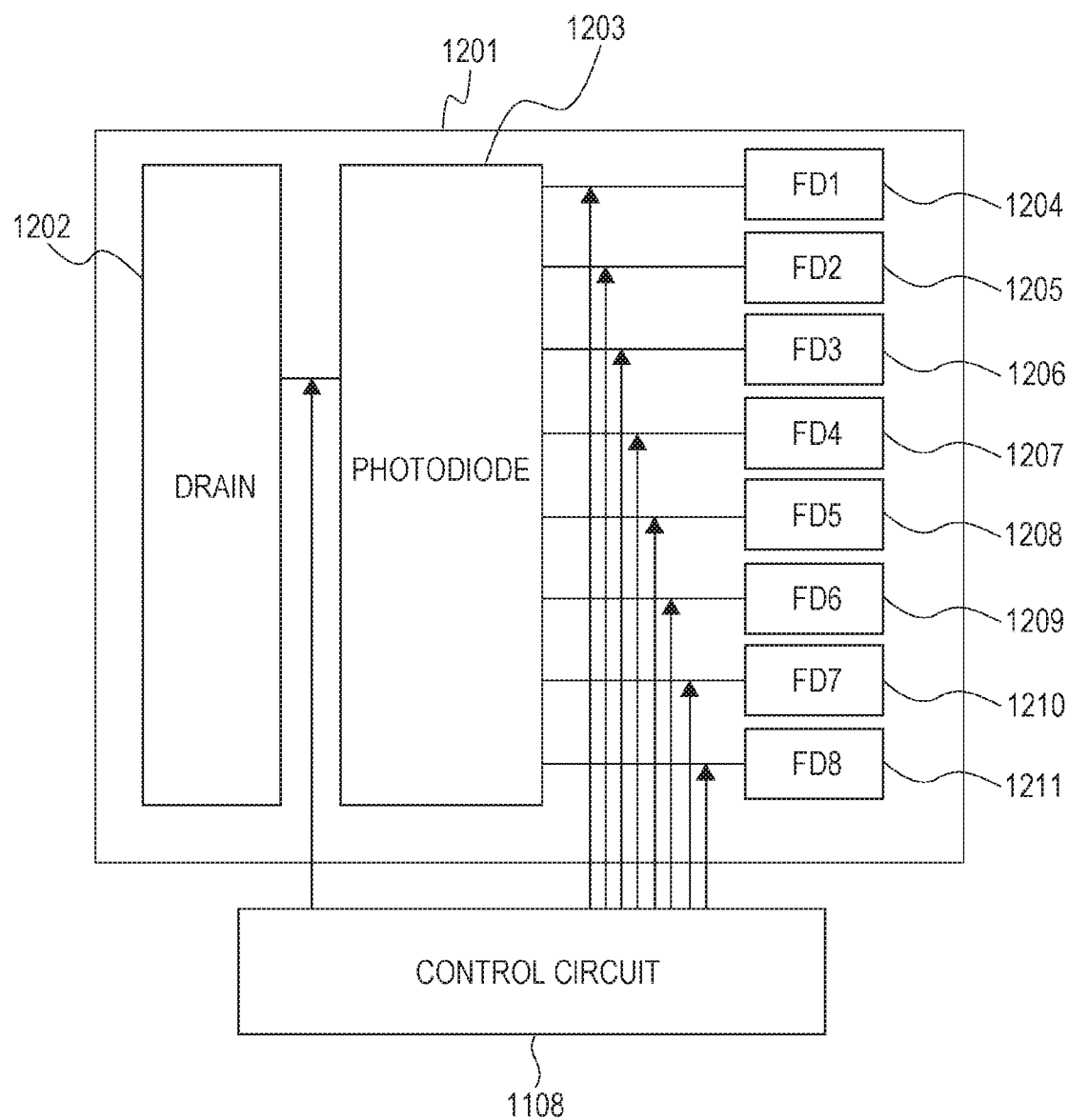
FIG. 13 is a drawing depicting an overview of a pixel configuration of an image sensor in embodiment 3 of the present disclosure.

FIG. 13 is a drawing depicting an overview of the pixel configuration of the image sensor 1106 in the present embodiment. The image sensor 1106 in the present embodiment has a large number of floating diffusion layers, and operates at a higher speed compared with the image sensor in embodiment 1. Hereinafter, a configuration and operation of the image sensor 1106 will be described.

A photoelectric conversion unit (photodiode) 1203 is arranged within a pixel 1201. The photodiode 1203 converts incident photons into signal electrons. The converted signal electrons are discharged to a signal charge discharge unit (drain) 1202, or are divided, at high speed, into eight floating diffusion layers (FD1 to FD8) 1204 to 1211 in accordance with control signals that are input from the control circuit 1108.

In the present embodiment, since the target is a light scattering body, the dividing is performed according to arrival time by means of the time-resolved function of the image sensor 1106, and light is thereby divided for each optical path length of the light that is scattered within the head.

Figure 14:
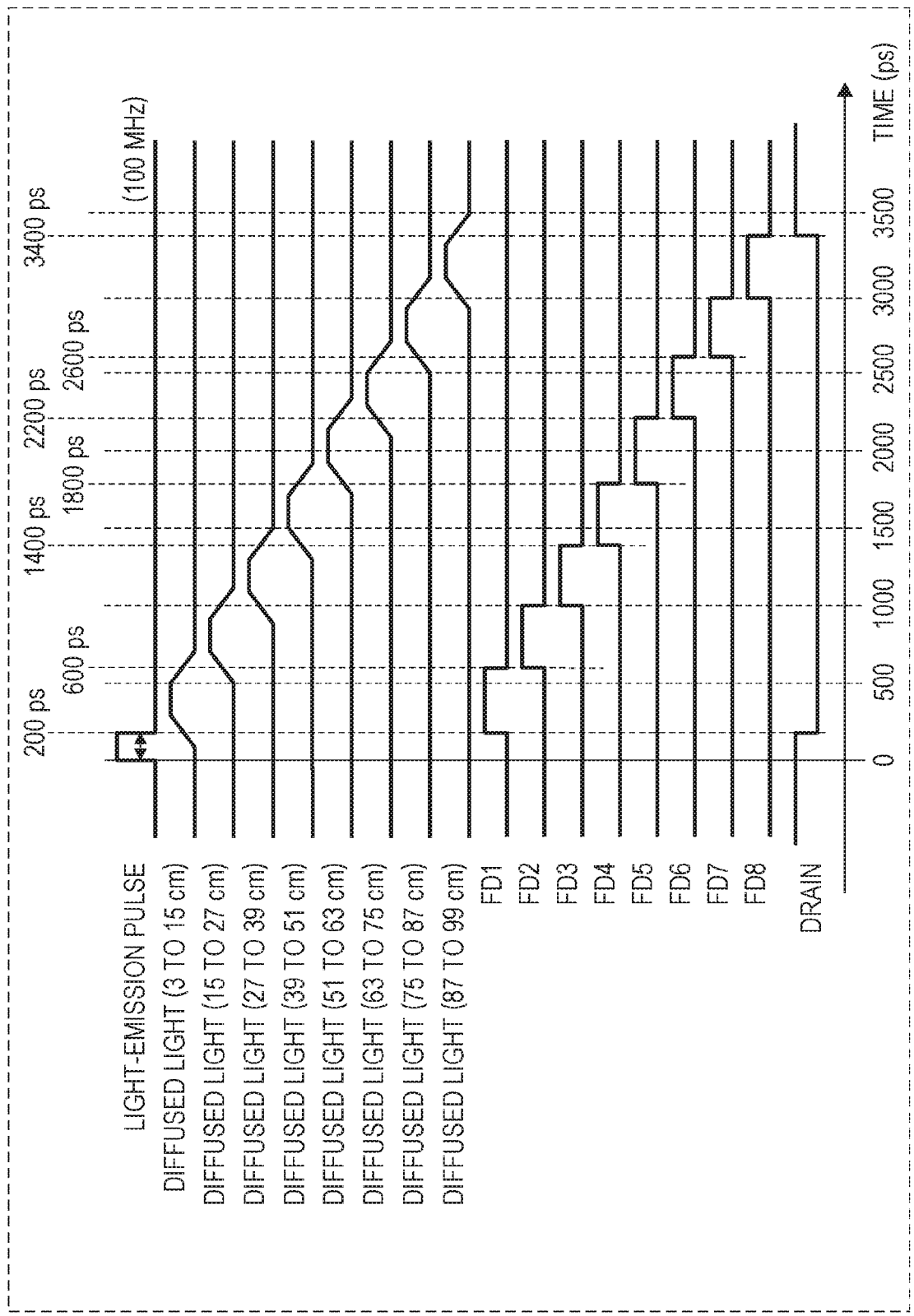
FIG. 14 is a drawing depicting timings of a light-emission pulse, diffused light of each distance range, signal accumulation pulses to eight floating diffusion layers, and a discharge pulse to a drain in embodiment 3 of the present disclosure.

FIG. 14 is a drawing depicting timings of a light-emission pulse, diffused light of each distance range, signal accumulation pulses to the eight floating diffusion layers, and a discharge pulse to the drain 1202 in the present embodiment. In the present embodiment, as an example, the maximum optical path length is set as 99 cm (converted value for a vacuum). The speed of light is 300,000 km per second, and therefore the time required for light to propagate the distance of 99 cm is 3300 picoseconds (ps). If the light-emission pulse width is set as 200 ps, the time required for one cycle is 3500 ps as depicted in FIG. 14, which is the timing at which a light component of the rear end of a light-emission pulse reaches the light-receiving surface of the image sensor 1106. In the present embodiment, in order to exclude the effect of light of a longer optical path length than the maximum optical path length of 99 cm, a margin period is set to 6500 ps, and the total time for one cycle is set as 10 ns. Consequently, the frequency of a light-emission pulse repeating cycle is the inverse thereof of 100 MHz.

In the case where a plurality of light sources are used, each light source may be controlled so as to emit light in this margin period. In the case where a large number of light sources are used, the margin period or the light emission frequency per one light source may be adjusted as required.

The abovementioned light-emission pulse timing and drive timing for the image sensor are examples and are not restricted to these examples. These numerical values may be appropriately set to optimal values in accordance with the optical path length within the living body, the target molecules, and the sensitivity of a light-receiving element.

Hereinafter, details of the operation depicted in FIG. 14 will be described. The light source 1104 emits light at a timing of 0 ps depicted in FIG. 14, and extinguishes at a timing of 200 ps in accordance with a control signal that is input from the control circuit 1108. At such time, the drain discharge pulse is set to ON in order to eliminate signal charge corresponding to leakage light that has entered from outside of the head and light having an optical path length of 3 cm or less that is outside of the measurement target range. During this time, unnecessary signal charge generated by the photodiode 1203 is discharged from the drain 1202.

Irradiated near-infrared light, as depicted in FIG. 14, is delayed according to the optical path lengths and is formed into a multiplex image that is encoded and diffracted by the image sensor 1106. This multiplex image is converted into signal charge by the photodiode 1203.

In principle, components of light having an optical path length of less than 3 cm and components of light having an optical path length of 3 cm to 15 cm are included in crosstalk proportionate to a time corresponding to the light-emission pulse width of 200 ps. Therefore, in the present embodiment, the reception of light starts from a timing at which the crosstalk assumes a median value. Specifically, the reception of light starts from a timing of 200 ps obtained by adding 100 ps, which is half of the light-emission pulse width of 200 ps, from a timing of 100 ps at which components of diffused light (optical path length of 3 to 15 cm) start to reach the image formation surface of the image sensor 1106.

The control circuit 1108 sets the signal accumulation pulse for the first floating diffusion layer (FD1) 1204 to ON at the same time as setting the drain discharge pulse to OFF at the timing of 200 ps depicted in FIG. 14. The signal accumulation pulse for the first floating diffusion layer 1204 is then set to OFF at the timing of 600 ps, which is when the components of diffused light (optical path length of 3 to 15 cm) attenuate and result in a 50% amount of light. Signal charge is thereby transferred and accumulated in the first floating diffusion layer 1204. Similarly, the control circuit 1108 sequentially sets signal accumulation pulses for the second to eighth floating diffusion layers (FD2 to FD8) 1205 to 1211 to ON at the timings depicted in FIG. 14. Time-resolved signal charge that includes crosstalk proportionate to the light-emission pulse width of 200 ps is thereby sequentially transferred and accumulated in the first to eighth floating diffusion layers 1204 to 1211. The control circuit 1108 sets the drain discharge pulse to ON at the timing of 3400 ps at which the signal accumulation pulse for the eighth floating diffusion layer 1211 is set to OFF. Unnecessary signal charge due to light having an optical path length of 99 cm or more that is longer than the measurement optical path length is thereby discharged from the drain 1202.

By repeating the above series of operations several hundred thousand times to several trillion times as required in the frequency of 100 MHz, signal charge of one frame of the image sensor 1106 is accumulated. The number of times repeated is adjusted according to the light emission intensity of the light source 1104 and the sensitivity of the image sensor 1106. The near-infrared diffused light that returns from within the brain is extremely weak light, and therefore, by repeatedly performing this high-speed imaging synchronized with the laser light emission a considerable number of times, it is possible to compensate for a lack of sensitivity.

In the present embodiment, the number of time resolutions according to the plurality of floating diffusion layers is eight; however, it should be noted that the number of time resolutions may be designed as a number other than eight in accordance with the purpose.

Figure 15:
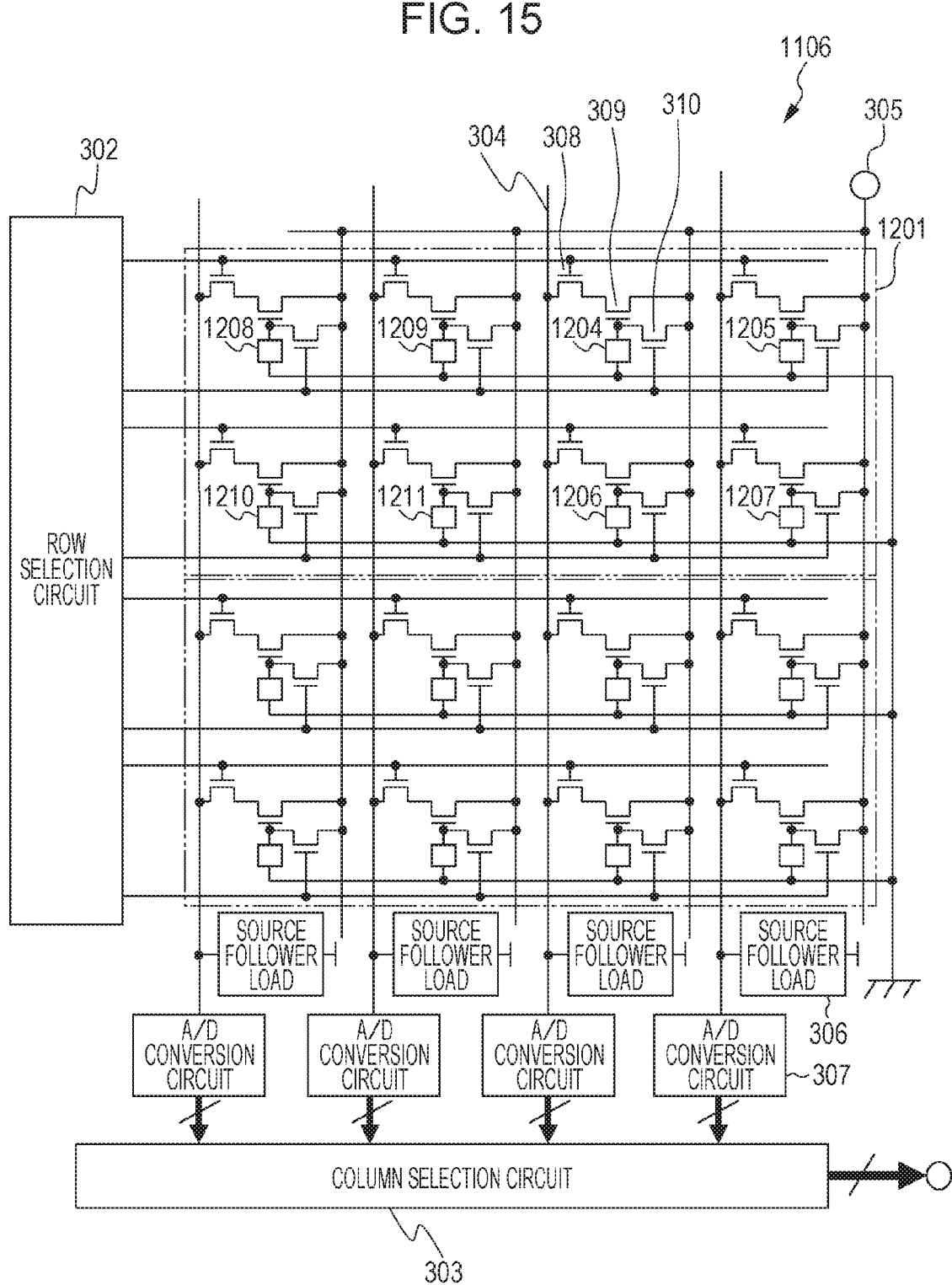
FIG. 15 is a drawing depicting an example of an overall configuration of the image sensor in embodiment 3 of the present disclosure.

FIG. 15 is a drawing depicting an example of an overall configuration of the image sensor 1106 in the present embodiment. A region surrounded by a two-dot chain line border in FIG. 15 corresponds to one pixel 1201. The pixel 1201 includes the eight floating diffusion layers 1204 to 1211. Signals accumulated in the eight floating diffusion layers 1204 to 1211 are treated as if they were signals of eight pixels of a general CMOS image sensor, and are output from the image sensor 1106.

The operation regarding the reading of a signal after the time-resolved imaging performed by this image sensor 1106 is the same as in embodiment 1 except for there being a large number of floating diffusion layers, and therefore a description thereof has been omitted.

Next, the operation performed by the signal processing circuit 1112 will be described. First, the wavelength band used in the present embodiment will be described.

Figure 16A:
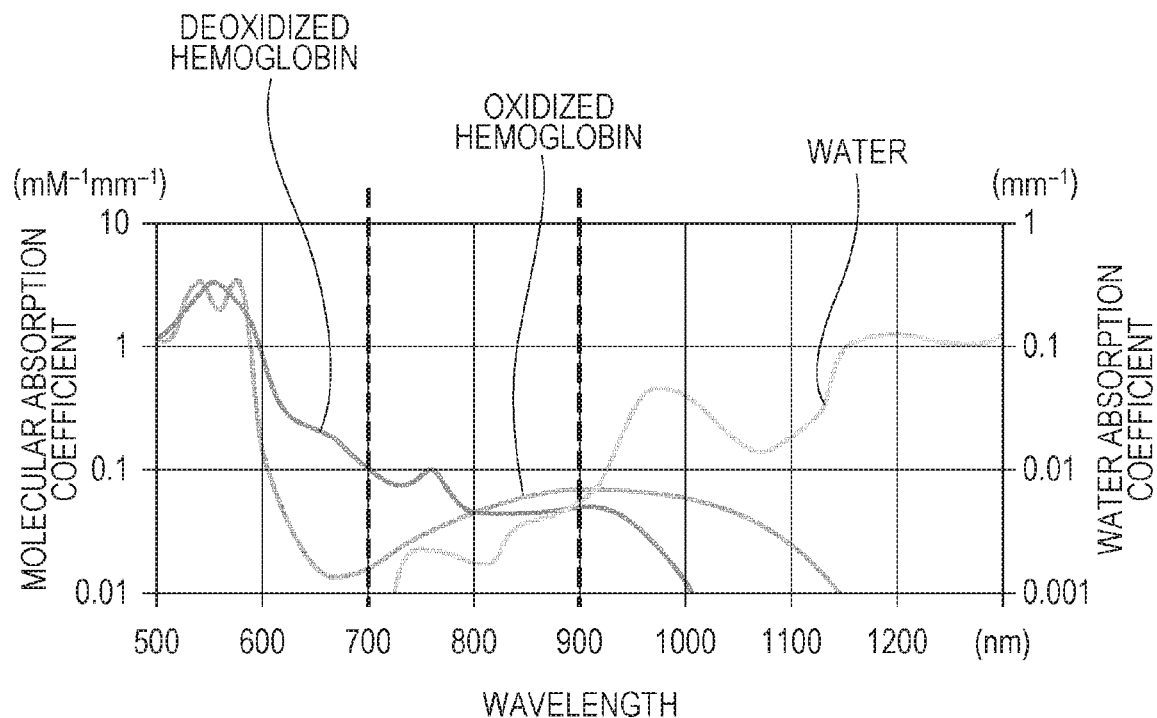
FIG. 16A is a graph depicting the wavelength dependency of absorption coefficients for oxidized hemoglobin, deoxidized hemoglobin, and water.
Figure 16B:
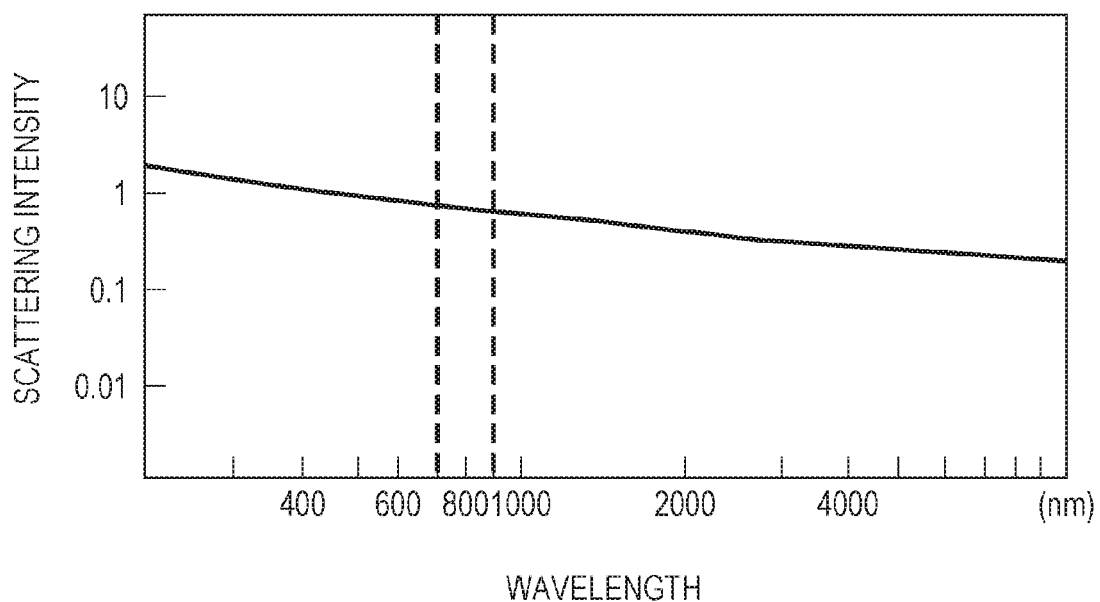
FIG. 16B is a graph depicting the wavelength dependency of the scattering coefficient of light within biological tissue.

FIG. 16A is a graph depicting the wavelength dependency of absorption coefficients for oxidized hemoglobin, deoxidized hemoglobin, and water. FIG. 16B is a graph depicting the wavelength dependency of the scattering coefficient of light within biological tissue. The wavelength band (700 to 900 nm) between the two dashed lines in the drawings is known as an optical tissue window, and has characteristics in that the absorption rate by the molecules within a living body is low. Near-infrared light having broad spectral characteristics of 700 to 900 nm irradiated at 100-MHz, 200-ps width pulses scatters and diffuses inside the head. At such time, light is absorbed in each wavelength in accordance with the absorption coefficients of oxidized hemoglobin and deoxidized hemoglobin inside the living body depicted in FIG. 16A. Some of the light that propagates without being absorbed reaches the light-receiving surface of the image sensor 1106 and is received. At a wavelength of 700 to 800 nm, the absorption coefficient of deoxidized hemoglobin is higher than the absorption coefficient of oxidized hemoglobin, and this relationship inverts at 800 to 900 nm. Therefore, the concentration information for these molecules is included as spectral characteristics information in the scattered light within the brain. In the present embodiment, the number of spectral separations of 20 bands is set for each wavelength band width of 10 nm. It should be noted that the number of spectral separations is not restricted to this example, and may be appropriately set according to the requirements of the application applied.

A first signal processing unit 1109 in the signal processing circuit 1112 separates, for each wavelength band, spectral multiplex images of multiple wavelengths in each of eight time-resolved images output from the image sensor 1106. This method is the same as in embodiments 1 and 2, and therefore a description thereof has been omitted here.

Next, a second signal processing unit 1110 performs signal processing for reconstructing a 3D image.

Figure 17:
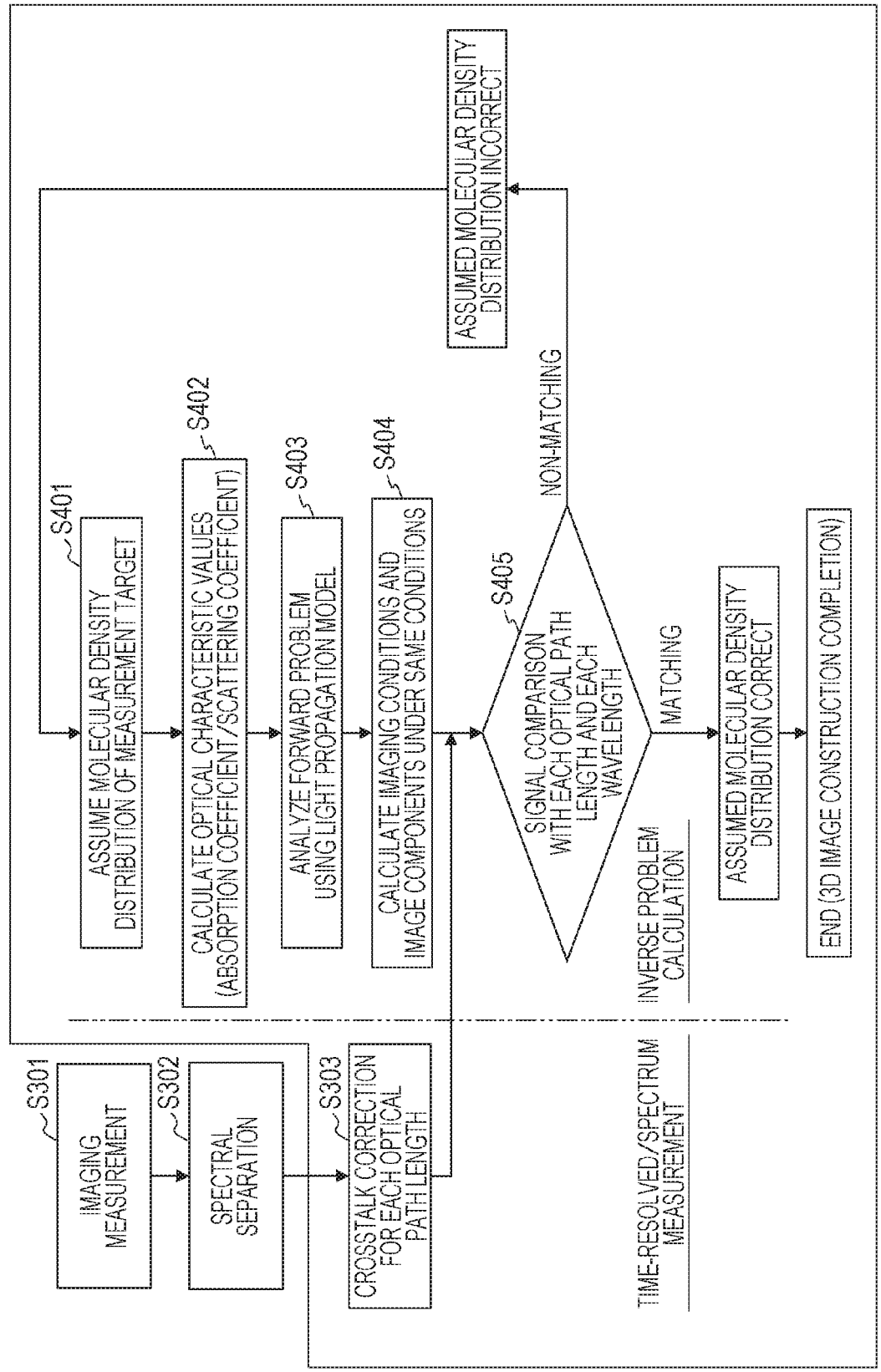
FIG. 17 is a flowchart depicting a signal processing flow in embodiment 3 of the present disclosure.

FIG. 17 is a flowchart depicting the flow of this signal processing. According to the aforementioned time-resolved imaging, eight 2D images corresponding to FD1 (3 to 15 cm), FD2 (15 to 27 cm), FD3 (27 to 39 cm), FD4 (39 to 51 cm), FD5 (51 to 63 cm), FD6 (63 to 75 cm), FD7 (75 to 87 cm), and FD8 (87 to 99 cm) are output from the image sensor 1106 (step S301). Due to the first signal processing unit 1109 performing processing for spectral separation, spectral images of 20 bands, for example, are generated for each optical path length (step S302). In other words, a total of 160 2D images of eight-optical path length, 20-band diffraction are generated from imaging measurement results for one frame, per one image sensor 1106.

Next, the second signal processing unit 1110 appropriately applies a high-pass enhancement filter to level changes for same pixel addresses between images of the optical path lengths. Thus, the effect of crosstalk generated due to the light-emission pulse time of the near-infrared laser pulse light source 1104 having a finite length (200 ps, for example), in other words, the effect that changes in pixel values of the same pixel address decrease, is corrected. The second signal processing unit 1110 compares the result of this correction as an imaging measurement result with a simulation result that is described later on.

Figure 18:
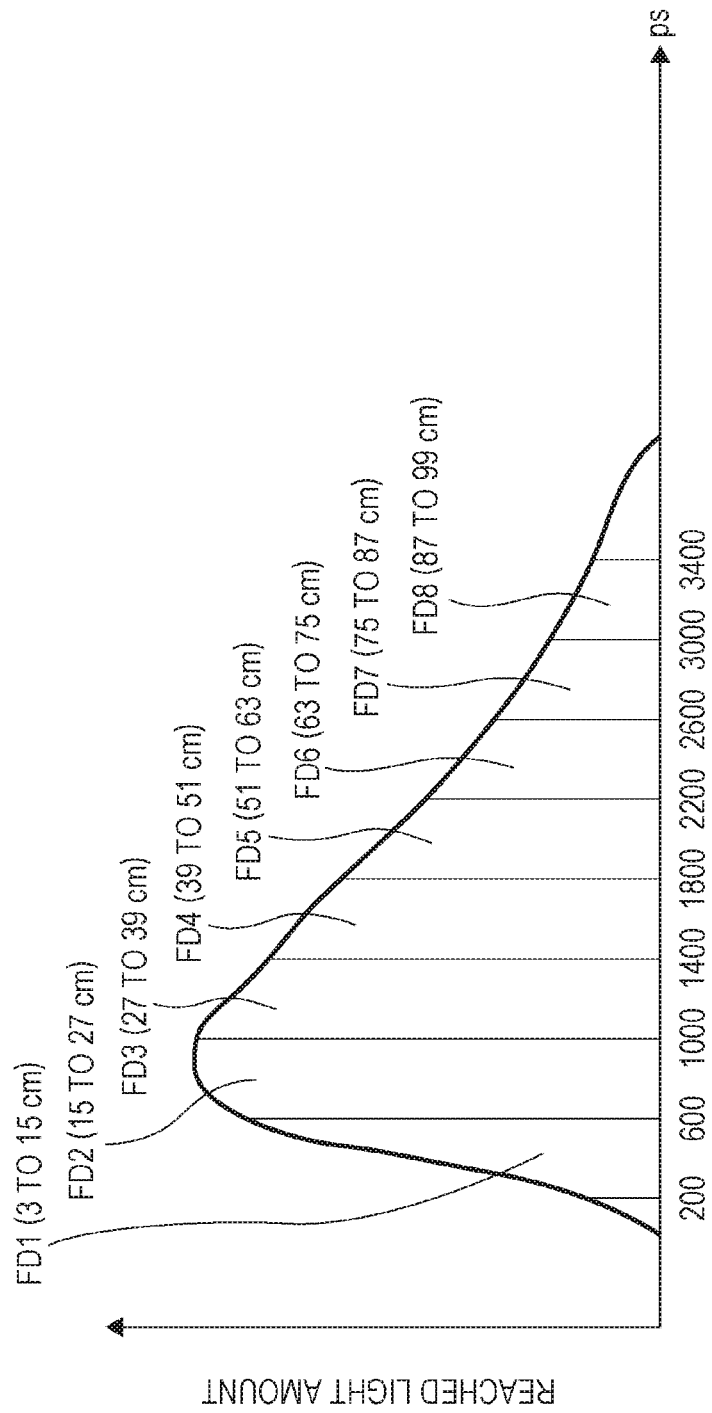
FIG. 18 is a drawing depicting an example of changes over time in the amount of light that reaches one pixel in embodiment 3 of the present disclosure.

FIG. 18 is a drawing depicting an example of changes over time in the amount of light that reaches one pixel. As depicted, light continuously reaches the one pixel in accordance with the optical path length from the light source 1104. An integrated value therefor is detected for each optical path length (FD1 to FD8). Therefore, in principle, crosstalk components are included in signals for each pixel. In step S303, processing for reducing the effect of this crosstalk is performed.

Next, the flow of the simulation depicted in FIG. 17 will be described.

Within biological tissue, near-infrared light scatters considerably, and absorption is relatively weak. Therefore, it is known that optical phenomena that occur within biological tissue can be approximated as light diffusion phenomena. The scattering pattern also becomes isotropic when the thickness of the biological tissue exceeds several mm, and the optical energy propagates in all directions in a diffusive manner. The intensity of scattering is represented by a scattering coefficient, and the intensity of absorption is represented by an absorption coefficient. The inverse of these coefficients represent distance. Light propagation within a living body can be expressed by an optical diffusion equation.

In the 3D image reconstruction algorithm indicated in FIG. 17, first, the molecular density distribution of oxidized hemoglobin, deoxidized hemoglobin, and the like within a living body is assumed (step S401). Next, a distribution of optical characteristic values (absorption coefficient and scattering coefficient) is calculated (step S402). Then, a forward problem analysis is performed, in which a model for light propagation within the living body is used to numerically solve the propagation of light (step S403). In addition, components of image signals of each optical path length and each wavelength are calculated under the same conditions as the imaging conditions (step S404). The result thereof is compared with a result obtained by imaging measurement (step S405). If everything matches, it is determined that the assumed molecular density distribution is correct, and that a 3D image has been reconstructed. If the results do not match, it is determined that the assumed molecular density is incorrect, the molecular density distribution is re-assumed, and the processing of steps S401 to S405 is executed once again. The second signal processing unit 1110 repeats this operation until the results match in step S405 (inverse problem).

The above processing is the same as the processing performed in general optical diffusion tomography.

The second signal processing unit 1110 generates and outputs an image depicting a blood state, on the basis of obtained results and information on the absorption spectra of oxidized hemoglobin and deoxidized hemoglobin depicted in FIG. 16A.

Furthermore, it is possible to simulate, in detail, the differences in the scattering coefficient for each wavelength depicted in FIG. 16B, and by using the result thereof, the precision with which the inverse problem is solved is improved. In the present embodiment, it is possible to obtain, for example, a 20-band spectral image by means of spectral compressed sensing for which a broad-band light source is used. In addition, by means of the time-resolved image sensor 1106, it is possible to obtain an image (frame) having sufficient spatial sampling points (number of pixels). As a result, it becomes possible to simultaneously satisfy an increase in the resolution of a desired 3D reconstruction image and a reduction in the measurement time.

Embodiment 4

Similar to embodiment 3, an imaging device of embodiment 4 is able to reconstruct the identification of molecules to be observed and the concentration distribution thereof as a 3D image, with a light scattering body such as a living body serving as a target.

Figure 19:
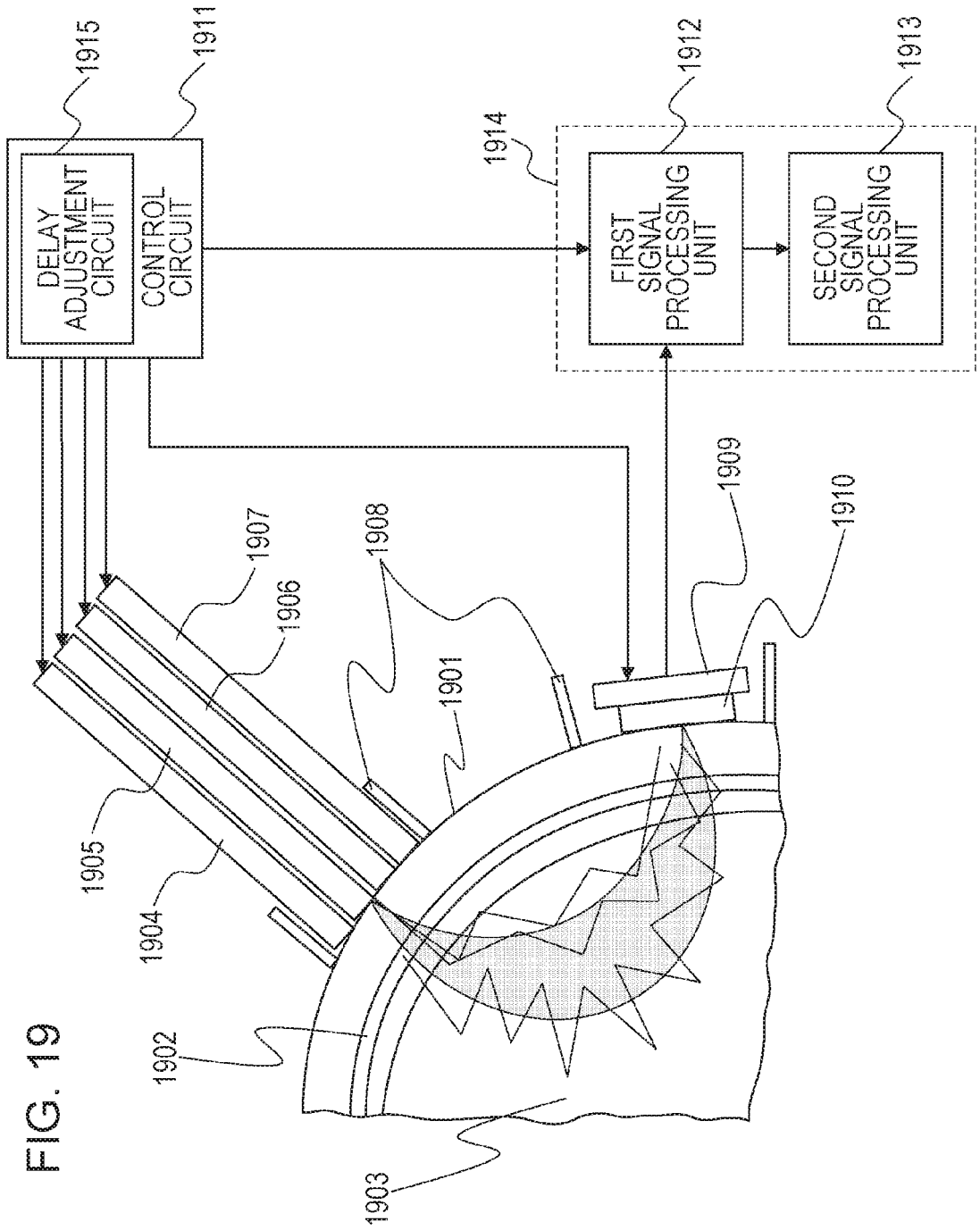
FIG. 19 is a drawing depicting a configuration of an imaging device in embodiment 4 of the present disclosure.

FIG. 19 is drawing depicting a schematic configuration of the imaging device of the present embodiment. The imaging device is provided with: a first near-infrared laser pulse light source 1904, a second near-infrared laser pulse light source 1905, a third near-infrared laser pulse light source 1906, and a fourth near-infrared laser pulse light source 1907 that emit pulsed light including mutually different wavelengths; an encoding spectroscopic element 1910; an image sensor 1909; a control circuit 1911 that includes a delay adjustment circuit 1915; and a signal processing circuit 1914 that includes a first signal processing unit 1912 and a second signal processing unit 1913. The imaging device of embodiment 4 is different from the imaging device of embodiment 3 in being provided with a plurality of light sources and including a control circuit and a delay adjustment circuit. An example is given in the present embodiment in which there are four light sources, but the number of light sources is not restricted to four.

Hereinafter, differences with the operation of the imaging device of embodiment 3 will be mainly described. The first near-infrared laser pulse light source 1904, the second near-infrared laser pulse light source 1905, the third near-infrared laser pulse light source 1906, and the fourth near-infrared laser pulse light source 1907 respectively irradiate pulsed light of a 750-nm wavelength, pulsed light of an 800-nm wavelength, pulsed light of an 850-nm wavelength, and pulsed light of a 900-nm wavelength toward brain tissue 1903, which is the detection target. This irradiation is repeatedly performed in short pulses in accordance with a control signal from the control circuit 1911.

The diffusion coefficient and scattering coefficient within the brain tissue 1903 for each pulsed light are different from each other due to the wavelengths being different. In order to eliminate this difference, the delay adjustment circuit 1915 within the control circuit 1911 performs minute adjustments on the light-emission timings of the first near-infrared laser pulse light source 1904, the second near-infrared laser pulse light source 1905, the third near-infrared laser pulse light source 1906, and the fourth near-infrared laser pulse light source 1907.

In the present embodiment, loss due to reflection by a head surface 1901 is reduced, and near-infrared light is efficiently guided into the brain, and therefore the first near-infrared laser pulse light source 1904, the second near-infrared laser pulse light source 1905, the third near-infrared laser pulse light source 1906, and the fourth near-infrared laser pulse light source 1907 may be used in close contact with the head surface 1901. Furthermore, reflection may be reduced using a gel sheet, a cream, or the like. In the example depicted in FIG. 19, light-blocking plates 1908 are used in order to cut leakage light from skin.

A portion of the irradiated short-pulse infrared light rays passes through the cranium 1902, is repeatedly absorbed and elastically scattered within the brain tissue 1903, and propagates while attenuating. A portion thereof once again passes through the cranium 1902, passes through the head surface 1901, reaches a light-receiving surface of the image sensor 1909 via the encoding spectroscopic element 1910, and photoelectric conversion is performed.

The layer configuration and time-resolved function of the image sensor 1909 are the same as those of the image sensor 1106 of embodiment 3, and therefore a description thereof has been omitted.

Next, the operation performed by the signal processing circuit 1914 will be described. First, the wavelength band used in the present embodiment will be described.

FIG. 16A is a graph depicting the wavelength dependency of absorption coefficients for oxidized hemoglobin, deoxidized hemoglobin, and water. FIG. 16B is a graph depicting the wavelength dependency of the scattering coefficient of light within biological tissue. Near-infrared light having wavelengths of 750 nm, 800 nm, 850 nm, and 900 nm irradiated at 100-MHz, 200-ps width pulses scatters and diffuses inside the head. At such time, light is absorbed in each wavelength in accordance with the absorption coefficients of oxidized hemoglobin and deoxidized hemoglobin inside the living body depicted in FIG. 16A. Some of the light that propagates without being absorbed reaches the light-receiving surface of the image sensor 1909 and is received. At a wavelength of 700 to 800 nm, the absorption coefficient of deoxidized hemoglobin is higher than the absorption coefficient of oxidized hemoglobin, and this relationship inverts at 800 to 900 nm. Therefore, the concentration information for these molecules is included as spectral characteristics information in the scattered light within the brain. In the present embodiment, the number of spectral separations of four bands of 750 nm, 800 nm, 850 nm, and 900 nm is set. It should be noted that the number of spectral separations is not restricted to this example, and may be appropriately set according to the requirements of the application applied.

The second signal processing unit 1913 performs signal processing for reconstructing a 3D image. FIG. 17 is a flowchart depicting the flow of this signal processing. According to the time-resolved imaging, eight 2D images corresponding to FD1 (3 to 15 cm), FD2 (15 to 27 cm), FD3 (27 to 39 cm), FD4 (39 to 51 cm), FD5 (51 to 63 cm), FD6 (63 to 75 cm), FD7 (75 to 87 cm), and FD8 (87 to 99 cm) are output from the image sensor 1909 (step S301). Due to the first signal processing unit 1912 performing processing for spectral separation, spectral images of four bands are generated for each optical path length (step S302). In other words, a total of 32 2D images of eight-optical path length, four-band diffraction are generated from imaging measurement results for one frame, per one image sensor 1909.

Next, the second signal processing unit 1913 appropriately applies a high-pass enhancement filter to level changes for same pixel addresses between images of the optical path lengths. Thus, the effect of crosstalk generated due to the light-emission pulse time of each near-infrared laser pulse light source having a finite length is corrected. The second signal processing unit 1913 compares the result of this correction as an imaging measurement result with a simulation result that is described later on.

Next, the flow of the simulation depicted in FIG. 17 will be described.

In the 3D image reconstruction algorithm indicated in FIG. 17, first, the molecular density distribution of oxidized hemoglobin, deoxidized hemoglobin, and the like within a living body is assumed (step S401). Next, a distribution of the absorption coefficient and scattering coefficient, which are optical characteristic values, is calculated (step S402). Then, a forward problem analysis is performed, in which a model for light propagation within the living body is used to numerically solve the propagation of light (step S403). In addition, components of image signals of each optical path length and each wavelength are calculated under the same conditions as the imaging conditions (step S404). The result thereof is compared with a result obtained by imaging measurement (step S405). If everything matches, it is determined that the assumed molecular density distribution is correct, and that a 3D image has been reconstructed. If the results do not match, it is determined that the assumed molecular density is incorrect, the molecular density distribution is re-assumed, and the processing of steps S401 to S405 is executed once again. The second signal processing unit 1913 repeats this operation until the results match in step S405.

The above processing is the same as the processing performed in general optical diffusion tomography.

The second signal processing unit 1913 generates and outputs an image depicting a blood state, on the basis of obtained results and information on the absorption spectra of oxidized hemoglobin and deoxidized hemoglobin depicted in FIG. 16A.

In the present embodiment, it is possible to obtain a four-band spectral image by means of spectral compressed sensing. In addition, by means of the image sensor 1909, it is possible to obtain an image having sufficient spatial sampling points. As a result, it becomes possible to simultaneously satisfy an increase in the resolution of a desired 3D reconstruction image and a reduction in the measurement time.

As described hereinabove, according to the embodiments of the present disclosure, it is possible to realize an imaging device that satisfies the three requirements of high time resolving, high resolution, and multiple wavelengths. In the case where a photographing target is a light-transmitting space, it is possible to perform range-gated imaging in which imaging is performed with targets being separated according to distance, and to obtain a 2D image for each wavelength corresponding to the range of the distance from the imaging device. Furthermore, it is possible to detect the type and concentration of gas molecules from wavelength shifts in light due to distinctive Raman scattering or wavelength shifts in light due to fluorescence in the gas molecules. By simultaneously performing range-gated imaging for each of a plurality of distance ranges, it is possible to realize the specifying of the type of a leaked gas and the non-contact detection of the three-dimensional distribution of the concentration of the gas, with a single imaging device.

Furthermore, in the case where the target is a light scattering body, by also performing highly time-resolved imaging of the order of picoseconds, 2D images separated for each optical path length and wavelength band within a scattering body are obtained. It is possible to detect the type and concentration of molecules within the scattering body on the basis of these 2D images and characteristics such as the distinctive absorption spectrum, scattering spectrum, or fluorescence spectrum of the molecules within the scattering body. In addition, it is possible to perform reconstruction by calculating a 3D distribution image of inside a detection-target scattering body from a plurality of 2D images of each optical path length. By using image information of a plurality of wavelength bands, there is an advantage in that it is possible to expect further improvement in the resolution of a generated 3D image, on the basis of differences in the scattering coefficient within the scattering body for each wavelength band.

What is claimed is:
1. An imaging apparatus for acquiring spectral separation images comprising:
an optical filter;
an image sensor including a first pixel and a second pixel and capturing an image; and
a signal processing circuit that is configured to perform separating the image captured by the image sensor into the spectral separation images using a compressed sensing algorithm, wherein
the optical filter includes filter regions arrayed two-dimensionally,
the filter regions include a first region and a second region,
a wavelength distribution of an optical transmittance of the first region has a first local maximum in a first wavelength band and a second local maximum in a second wavelength band that differs from the first wavelength band,
a wavelength distribution of an optical transmittance of the second region has a third local maximum in a third wavelength band and a fourth local maximum in a fourth wavelength band that differs from the third wavelength band,
the third wavelength band differs from both the first wavelength band and the second wavelength band, the first pixel receives light of the first wavelength band which has passed through the first region and light of the second wavelength band which has passed through the first region, and the second pixel receives light of the third wavelength band which has passed through the second region and light of the fourth wavelength band which has passed through the second region.

2. The imaging apparatus according to claim 1,
wherein each of optical transmittances at the first local maximum, the second local maximum, the third local maximum, and the fourth local maximum is not less than 0.5.

3. The imaging apparatus according to claim 1, wherein
each of the first region and the second region includes a multilayer film, and
at least one selected from the group consisting of a thickness and a layering order of the multilayer film is different for each of the first region and the second region.

4. The imaging apparatus according to claim 1, wherein a two-dimensional distribution of optical transmittance of the filter regions is a random distribution or a quasi-random distribution.

5. The imaging apparatus according to claim 1, wherein
the wavelength distribution of the optical transmittance of the first region has at least four local maxima, the at least four local maxima including the first local maximum and the second local maximum, and
the third wavelength band differs from each of the wavelength bands of the at least four local maxima in the first region.

6. The imaging apparatus according to claim 1, further comprising:
a light source that irradiates excitation light toward a target; and
an excitation light cut filter that cuts wavelength components of the excitation light.

* * * * *